(12) United States Patent
Kim et al.

(10) Patent No.: US 11,335,857 B2
(45) Date of Patent: May 17, 2022

(54) ORGANIC ELECTROLUMINESCENCE DEVICE AND DISPLAY DEVICE INCLUDING THE SAME

(71) Applicant: Samsung Display Co., Ltd., Yongin-Si (KR)

(72) Inventors: Seulong Kim, Cheonan-si (KR); Pilgu Kang, Bucheon-si (KR); Jiyoung Kwon, Uijeongbu-si (KR); Taekyung Kim, Yongin-si (KR); Soon-Chul Chang, Seoul (KR)

(73) Assignee: SAMSUNG DISPLAY CO., LTD., Yongin-Si (KR)

( * ) Notice: Subject to any disclaimer, the term of this patent is extended or adjusted under 35 U.S.C. 154(b) by 377 days.

(21) Appl. No.: 16/677,576

(22) Filed: Nov. 7, 2019

(65) Prior Publication Data
US 2020/0220082 A1 Jul. 9, 2020

(30) Foreign Application Priority Data

Jan. 9, 2019 (KR) .......................... 10-2019-0002844

(51) Int. Cl.
*H01L 51/50* (2006.01)
*H01L 51/00* (2006.01)
(Continued)

(52) U.S. Cl.
CPC .......... *H01L 51/0052* (2013.01); *C07C 15/28* (2013.01); *C07D 213/06* (2013.01);
(Continued)

(58) Field of Classification Search
None
See application file for complete search history.

(56) References Cited

U.S. PATENT DOCUMENTS 7,592,075 B2   9/2009 Oshiyama et al.
8,883,323 B2  11/2014 Kawamura et al.
(Continued)

FOREIGN PATENT DOCUMENTS

EP   2 963 032        1/2016
JP   2010-0260674 A  11/2010
(Continued)

*Primary Examiner* — Gregory D Clark
(74) *Attorney, Agent, or Firm* — Kile Park Reed & Houtteman PLLC

(57) ABSTRACT

Provided are an organic electroluminescence device and a display device including the same. The organic electroluminescence device includes a polycyclic compound represented by Formula 1 in a hole blocking layer and at least one of a first light emitting layer and an electron transport layer, wherein each of $Y_1$ to $Y_5$ and $Y_{11}$ to $Y_{15}$ is independently CH or N, at least four of $Y_1$ to $Y_5$ are CH, at least four of $Y_{11}$ to $Y_{15}$ are CH, and $R_1$, $R_2$, and $R_3$ are as disclosed in the description.

20 Claims, 12 Drawing Sheets

[Formula 1]

(51) Int. Cl.
*C07C 15/28* (2006.01)
*C07D 213/06* (2006.01)
*C09K 11/06* (2006.01)
*H01L 27/32* (2006.01)
*H01L 51/52* (2006.01)

(52) U.S. Cl.
CPC .......... *C09K 11/06* (2013.01); *H01L 51/0058* (2013.01); *H01L 51/0067* (2013.01); *C07C 2603/24* (2017.05); *C09K 2211/1007* (2013.01); *C09K 2211/1011* (2013.01); *C09K 2211/1018* (2013.01); *H01L 27/322* (2013.01); *H01L 51/5004* (2013.01); *H01L 51/5016* (2013.01); *H01L 51/5044* (2013.01); *H01L 51/5072* (2013.01); *H01L 51/5096* (2013.01); *H01L 51/5268* (2013.01); *H01L 2251/5369* (2013.01); *H01L 2251/552* (2013.01)

(56) References Cited

U.S. PATENT DOCUMENTS

| 10,069,077 | B2 | 9/2018 | Park et al. |
| 2006/0110622 | A1 | 5/2006 | Uchida et al. |
| 2012/0279645 | A1 | 11/2012 | Inokuchi et al. |
| 2016/0056386 | A1 | 2/2016 | Lee et al. |
| 2018/0047913 | A1* | 2/2018 | Ono ..................... H01L 51/008 |

FOREIGN PATENT DOCUMENTS

| KR | 10-0672536 B1 | 1/2007 |
| KR | 10-1482362 B1 | 1/2015 |
| KR | 10-2016-0031651 A | 3/2016 |
| KR | 10-2017-0038776 A | 4/2017 |

* cited by examiner

ORGANIC ELECTROLUMINESCENCE DEVICE AND DISPLAY DEVICE INCLUDING THE SAME

CROSS-REFERENCE TO RELATED APPLICATIONS

This U.S. non-provisional patent application claims priority under 35 U.S.C. § 119 to Korean Patent Application No. 10-2019-0002844, filed on Jan. 9, 2019, the entire contents of which are hereby incorporated by reference.

BACKGROUND

The present disclosure relates to an organic electroluminescence device and a display device including the same.

As an image display device, an organic electroluminescence device has been actively developed. An organic electroluminescence device is different from a liquid crystal display device and the like in that it is a so-called self-luminescence display device which realizes display by recombining holes and electrons injected from a first electrode and a second electrode in a light emitting layer to emit light from a light emitting material which is an organic compound included in the light emitting layer.

As an organic electroluminescence device, for example, an organic device composed of a first electrode, a hole transport layer disposed on the first electrode, a light emitting layer disposed on the hole transport layer, an electron transport layer disposed on the light emitting layer, and a second electrode disposed on the electron transport layer are known. From the first electrode, a hole is injected, and the injected hole moves through the hole transport layer and is injected to the light emitting layer. Meanwhile, from the second electrode, an electron is injected, and the injected electron moves through the electron transport layer and is injected to the light emitting layer. The hole and the electron both injected to the light emitting layer are recombined to generate an exciton in the light emitting layer. An organic electroluminescence device emits light using light generated when the exciton falls to a ground state again.

In recent years, in order to implement a high-efficiency organic electroluminescence device, techniques for phosphorescence light emission using triplet state energy or delayed fluorescence light emission using triplet-triplet annihilation (TTA) in which a singlet exciton is generated by the collision of a triplet exciton have been developed.

Also, in order to improve the lifespan of an organic electroluminescence device, studies on organic electroluminescence device materials have been actively conducted.

SUMMARY

The present disclosure provides an organic electroluminescence device including a polycyclic compound and a display device including the organic electroluminescence device.

An embodiment of the inventive concept provides an organic electroluminescence device including a first electrode, a second electrode, and a first light emitting unit. In an embodiment, the second electrode may be disposed on the first electrode. In an embodiment, the first light emitting unit may be disposed between the first electrode and the second electrode.

In an embodiment, the first light emitting unit may include a first hole transport region, a first light emitting layer, and a first electron transport region. In an embodiment, the first hole transport region may be disposed on the first electrode. In an embodiment, the first light emitting layer may be disposed on the first hole transport region and include a host and a dopant. In an embodiment, the first electron transport region may be disposed on the first light emitting layer and include a hole blocking layer and an electron transport layer disposed on the hole blocking layer.

In an embodiment, the hole blocking layer, and at least one layer of the first light emitting layer or the electron transport layer may include a polycyclic compound represented by Formula 1 below.

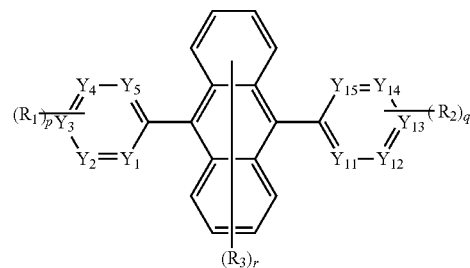

[Formula 1]

In Formula 1, each of $Y_1$ to $Y_5$ and $Y_{11}$ to $Y_{15}$ may independently be CH or N. In an embodiment, at least four of $Y_1$ to $Y_5$ may be CH. In an embodiment, at least four of $Y_{11}$ to $Y_{15}$ may be CH. In an embodiment, $R_1$ to $R_3$ may each be independently a substituted or unsubstituted alkyl group having 2 to 20 carbon atoms, a substituted silyl group, a substituted boron group, a substituted or unsubstituted aryl group having 6 to 30 ring-forming carbon atoms, or a substituted or unsubstituted heteroaryl group having 3 to 30 ring-forming carbon atoms, or may form a ring by being coupled to an adjacent group. In an embodiment, each of p and q may independently be an integer of 1 to 5, and r may be an integer of 0 to 8.

In an embodiment, the host may include the polycyclic compound. In an embodiment, the hole blocking layer may only include the polycyclic compound. In an embodiment, the first light emitting layer, the hole blocking layer, and the electron transport layer may include the polycyclic compound. In an embodiment, the difference in HOMO energy level and the difference in LUMO energy level between the host and the polycyclic compound may each be 0 eV to 0.1 eV.

In an embodiment, the hole mobility of the polycyclic compound may be 0 cm²/Vs to 10' cm²/Vs. In an embodiment, the triplet energy level of the polycyclic compound may be 1.6 eV to 1.8 eV. In an embodiment, the difference in triplet energy level between the host and the polycyclic compound may be 0 eV to 0.2 eV.

In an embodiment, in Formula 1, at least one among $R_1$ to $R_3$ may be a substituted or unsubstituted pyridine group, a substituted or unsubstituted bipyridine group, a substituted or unsubstituted pyrimidine group, a substituted or unsubstituted triazine group, a substituted or unsubstituted quinoline group, a substituted or unsubstituted quinazoline group, a substituted or unsubstituted quinoxaline group, a substituted or unsubstituted phthalazine group, a substituted or unsubstituted indole group, a substituted or unsubstituted pyrazine group, a substituted or unsubstituted pyridazine group, a substituted or unsubstituted thiophene group, a substituted or unsubstituted oxazole group, a substituted or unsubstituted thiazole group, or a substituted or unsubstituted pyrazole group.

In an embodiment, the light emitting layer may emit light having a wavelength region of 440 nm to 490 nm.

In an embodiment, the organic electroluminescence device may further include at least one light emitting unit disposed on the first light emitting unit. In an embodiment, the at least one light emitting unit may include a second hole transport region, a second light emitting layer, and a second electron transport region. In an embodiment, the second hole transport region may be disposed on the first light emitting unit. In an embodiment, the second light emitting layer may be disposed on the second hole transport region. In an embodiment, the second electron transport region may be disposed between the second light emitting layer and the second electrode. In an embodiment, the first light emitting unit and the at least one light emitting unit may emit blue light.

In an embodiment, the polycyclic compound may include at least one among the compounds represented by Compound Group 1 below.

[Compound Group 1]

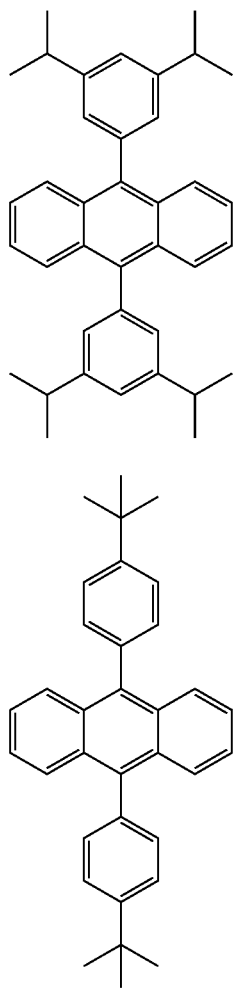

1

2

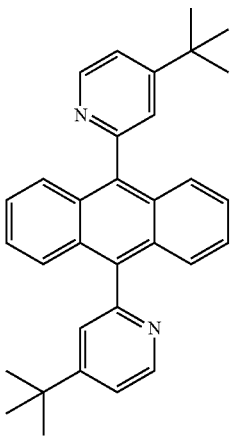

3

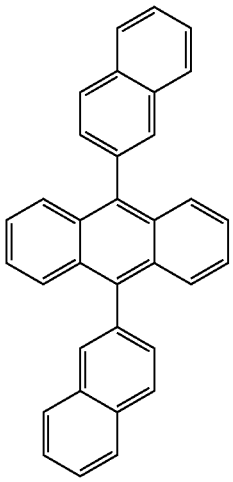

4

In an embodiment of the inventive concept, an organic electroluminescence device includes a first electrode, a hole transport region, a light emitting layer, an electron transport region, and a second electrode.

In an embodiment, the hole transport region may be disposed on the first electrode. In an embodiment, the light emitting layer may be disposed on the hole transport region. In an embodiment, the electron transport region may be disposed on the light emitting layer. In an embodiment, the electron transport region may include a hole blocking layer and an electron transport layer disposed on the hole blocking layer. In an embodiment, the second electrode may be disposed on the electron transport region.

In an embodiment, the hole blocking layer and the electron transport layer may include a polycyclic compound represented by Formula 1.

In an embodiment, the light emitting layer may include a host and a dopant. In an embodiment, the difference in HOMO energy level and the difference in LUMO energy level between the host and the polycyclic compound may each be 0 eV to 0.1 eV.

In an embodiment, the hole blocking layer may only include the polycyclic compound, and the electron transport layer may further include the polycyclic compound and at least one electron transport material.

In an embodiment of the inventive concept, a display device includes a light emitting element layer. The light emitting element layer may include a plurality of organic electroluminescence devices.

In an embodiment, an organic electroluminescent device may include a first electrode, a second electrode, and a plurality of organic layers. In an embodiment, the second electrode may be disposed on the first electrode. In an embodiment, the plurality of organic layers may be disposed between the first electrode and the second electrode.

In an embodiment, the plurality of organic layers may include a hole transport region, a first light emitting layer, and an electron transport region. In an embodiment, the hole transport region may be disposed on the first electrode. In an embodiment, the first light emitting layer may be disposed on the hole transport region. In an embodiment, the electron transport region may be disposed on the first light emitting layer and include a hole blocking layer and an electron transport layer. In an embodiment, the electron transport layer may be disposed on the hole blocking layer. In an embodiment, the hole blocking layer and the electron transport layer may include a polycyclic compound represented by Formula 1.

In an embodiment, the organic layers further include at least one light emitting layer disposed between the first electron transport region and the second electrode.

In an embodiment, a light conversion layer disposed on the light emitting element layer may be further included. In an embodiment, the light emitting element layer may emit blue light. In an embodiment, the light conversion layer may include a first light conversion part, a second light conversion part, and a third light conversion part. In an embodiment, the first light conversion part may absorb blue light and emit green light. In an embodiment, the second light conversion part may absorb blue light and emit red light. In an embodiment, the third light conversion layer may transmit blue light. In an embodiment, the first light conversion part may include a first quantum dot light emitting body which absorbs blue light and emits red light. In an embodiment, the second light conversion part may include a second quantum dot light emitting body which changes the wavelength of blue light and emits red light. In an embodiment, the third light conversion part may include a base resin and a scattering body dispersed in the base resin.

In an embodiment, each of the hole transport region, the first light emitting layer, and the electron transport region may be one layer in the light emitting element layer.

BRIEF DESCRIPTION OF THE FIGURES

The accompanying drawings are included to provide a further understanding of the inventive concept, and are incorporated in and constitute a part of this specification. The drawings illustrate exemplary embodiments of the inventive concept and, together with the description, serve to explain principles of the inventive concept. In the drawings.

DETAILED DESCRIPTION

Figure 1:
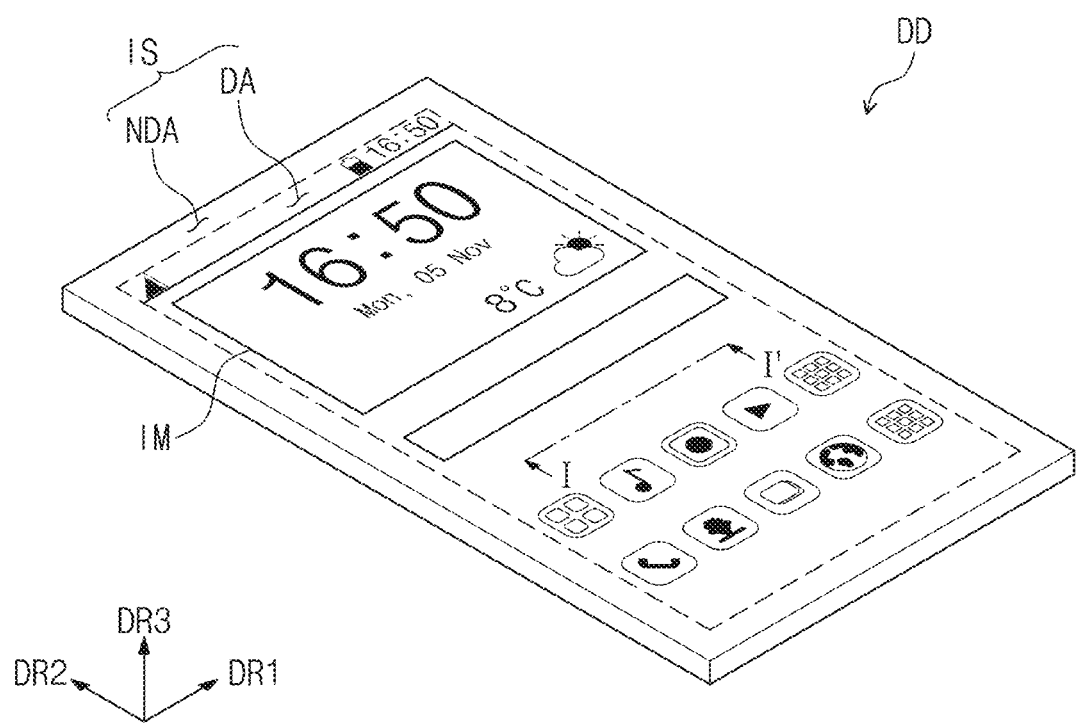
FIG. 1 is a perspective view of a display device according to an embodiment of the inventive concept.

In the present disclosure, when an element (or a region, a layer, a portion, etc.) is referred to as being "on," "connected to," or "coupled to" another element, it means that the element may be directly disposed on/connected to/coupled to the other element, or that a third element may be disposed therebetween.

Like reference numerals refer to like elements. Also, in the drawings, the thickness, the ratio, and the dimensions of elements are exaggerated for an effective description of technical contents.

The term "and/or" includes all combinations of one or more of which associated configurations may define.

It will be understood that, although the terms "first", "second", etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the inventive concept. The terms of a singular form may include plural forms unless the context clearly indicates otherwise.

In addition, terms such as "below," "lower," "above," "upper," and the like are used to describe the relationship of the configurations shown in the drawings. The terms are used as a relative concept and are described with reference to the direction indicated in the drawings.

Unless otherwise defined, all terms (including technical and scientific terms) used herein have the same meaning as commonly understood by one of ordinary skill in the art to which the inventive concept pertains. It is also to be understood that terms defined in commonly used dictionaries should be interpreted as having meanings consistent with the meanings in the context of the related art, and are expressly defined herein unless they are interpreted in an ideal or overly formal sense.

It should be understood that the terms "comprise", or "have" are intended to specify the presence of stated features, integers, steps, operations, elements, components, or combinations thereof in the disclosure, but do not preclude the presence or addition of one or more other features, integers, steps, operations, elements, components, or combinations thereof.

Hereinafter, an organic electroluminescence device OLED according to an embodiment of the inventive concept will be described with reference to the accompanying drawings.

FIG. 1 is a perspective view of a display device DD according to an embodiment of the inventive concept. As shown in FIG. 1, the display device DD may display an image IM through a display surface IS. The display surface IS is parallel to a plane defined by a first direction axis DR1 and a second direction axis DR2. The direction that is normal to the display surface IS, that is, the thickness direction of the display device DD, is indicated by a third direction axis DR3. The display surface IS may include a display region DA and a non-display region NDA.

The display region DA may be a region on which the image IM is displayed. The non-display region NDA may be a region on which the image IM is not displayed. In an embodiment, the non-display region NDA may be omitted.

Figure 2:
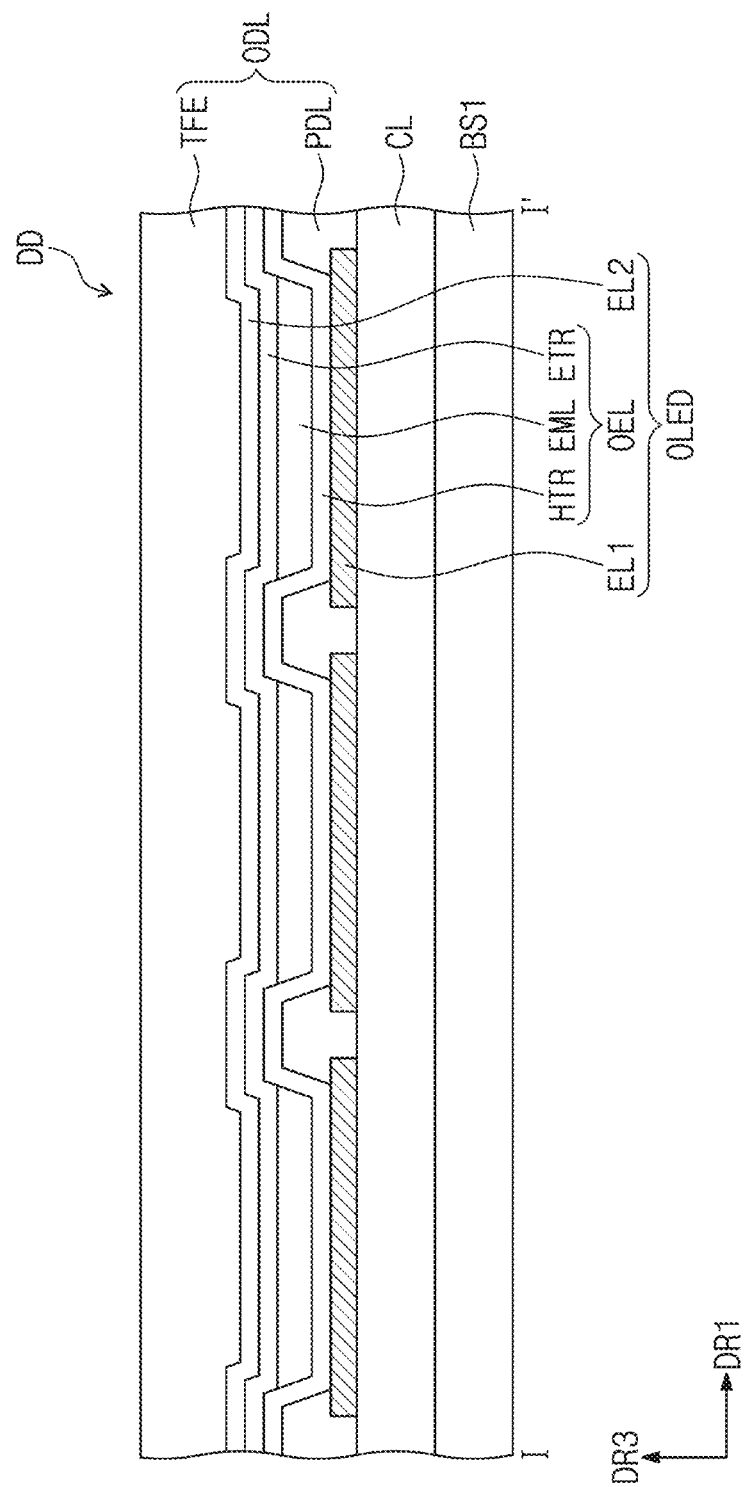
FIG. 2 shows a portion of a cross-section taken along line I-I' of FIG. 1.

FIG. 2 shows a portion of a cross-section taken along line I-I' of FIG. 1. FIG. 2 is simply shown in order to describe the disposal relationship among components constituting the display device DD.

The display device DD may include a first base substrate BS1, a circuit layer CL, and a light emitting element layer ODL. The light emitting element layer ODL may include a plurality of organic electroluminescence devices OLED, a plurality of pixel defining layers PDL, and a thin film encapsulation layer TEF. On first base substrate BS1, the circuit layer CL is disposed, and on the circuit layer CL, the light emitting element layer ODL may be disposed. On the circuit layer CL, the plurality of organic electroluminescence devices OLED may be disposed, and on the organic electroluminescence devices OLED, the thin film encapsulation layer TFE may be disposed. Although not shown, the display device DD may further include other components. For example, a glass substrate (not shown) or a cover substrate (not shown) may be further disposed on the thin film encapsulation layer TFE.

The first base substrate BS1 may be a silicon substrate, a plastic substrate, a glass substrate, an insulation film, or a disposed structural body including a plurality of insulation layers.

The circuit layer CL may include a plurality of transistors (not shown). Each of the organic electroluminescence devices OLED may be connected to each of the plurality of transistors (not shown) to receive a signal.

The respective organic electroluminescence devices OLED may be separated by the plurality of pixel defining layers PDL and may be spaced apart from each other on a plane. In the present specification, "on a plane" may mean that the display device DD is viewed in the third direction DR3 (thickness direction).

Each of the organic electroluminescence devices OLED may include a first electrode EL1, a second electrode EL2 disposed on the first electrode EL1, and a plurality of organic layer OEL disposed between the first electrode EL1 and the second electrode EL2. The plurality of organic layers OEL may include a hole transport region HTR, a light emitting layer EML disposed on the hole transport region HTR, and an electron transport region ETR disposed on the light emitting layer EML.

The hole transport region HTR and the electron transport region ETR are illustrated as a common layer, that is, one layer, disposed in the plurality of organic electroluminescence devices. However, the embodiment of the inventive concept is not limited thereto. For example, at least one of the hole transport region HTR and the electron transport region ETR may be disposed to be separated by the pixel defining layers PDL, respectively.

The light emitting layer EML is illustrated as being separately disposed in each of the organic electroluminescence devices. However, the embodiment of the inventive concept is not limited thereto. The light emitting layer EML may be disposed as a common layer, that is, one layer, in the organic electroluminescent devices OLED.

The pixel defining layer PDL is disposed between the first electrodes ELL and may overlap at least a portion of the first electrodes EL1. The pixel defining layer PDL may be formed of a polymer resin or an inorganic material. Also, the pixel defining layer PDL may be formed by further including an inorganic material in addition to a polymer resin. Meanwhile, the pixel defining layer PDL may be formed by including a light absorbing material, or may be formed by including a black pigment or a black dye.

The thin film encapsulation layer TFE may directly cover the second electrode EL2. The thin film encapsulation layer TFE may include an organic material layer containing an organic material and an inorganic material layer containing an inorganic material. In an embodiment, a capping layer (not shown) for covering the second electrode EL2 may be further disposed. At this time, the thin film encapsulation layer TFE may directly cover the capping layer.

FIG. 3 to FIG. 6 are cross-sectional views schematically showing organic electroluminescence devices OLED and OLED-1 according to an embodiment of the inventive concept.

Figure 3:
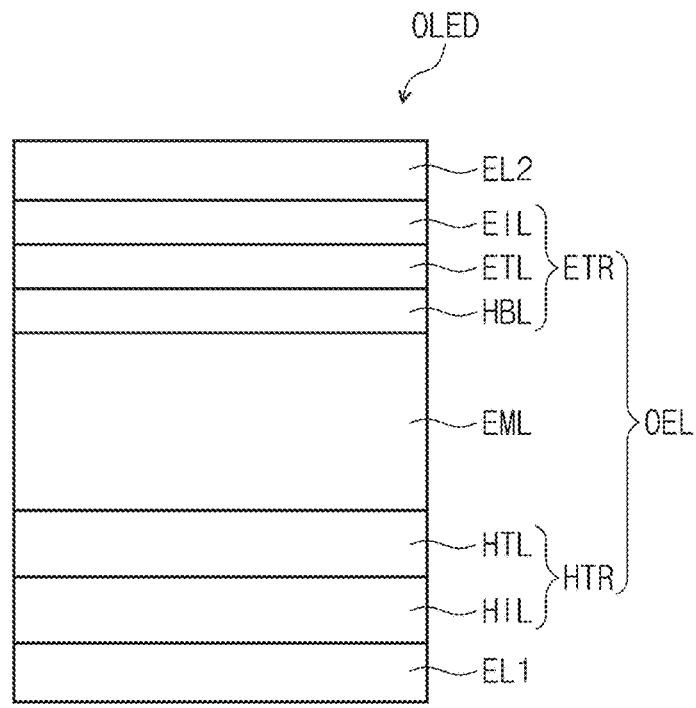
FIG. 3, FIG. 4, FIG. 5, and FIG. 6 are a cross-sectional views schematically showing an organic electroluminescence device according to an embodiment of the inventive concept.

Referring to FIG. 3, the hole transport region HTR may include a hole injection layer HIL and a hole transport layer HTL. The electron transport region ETR may include a hole blocking layer HBL, an electron transport layer ETL, and an electron injection layer EIL.

In the organic electroluminescence device OLED of an embodiment, the hole blocking layer HBL and at least one layer of the light emitting layer EML and the electron transport layer ETL may include a polycyclic compound of an embodiment to be described later. That is, in an embodiment, the hole blocking layer HBL may include the polycyclic compound of an embodiment, and at least one layer of the light emitting layer EML and the electron transport layer ETL may include the polycyclic compound of an embodiment.

Figure 4:
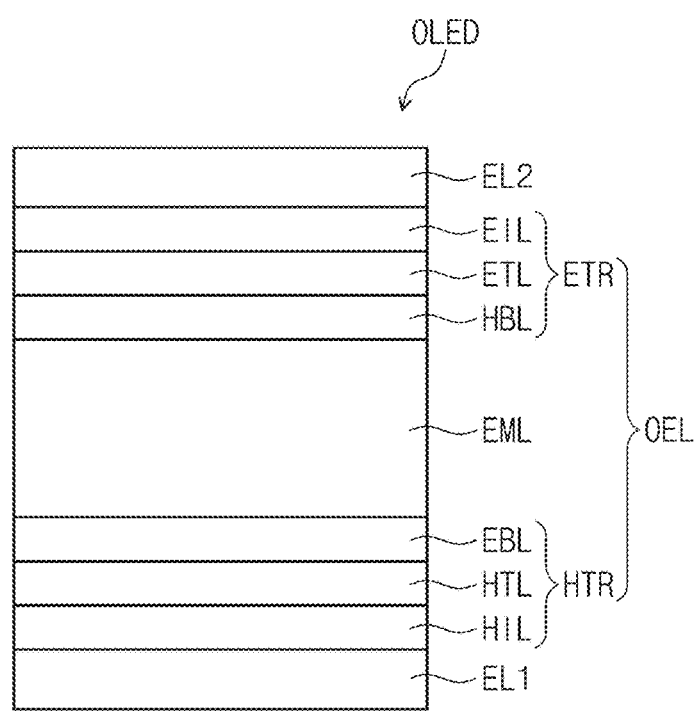

When compared to FIG. 3, FIG. 4 shows a cross-section of the organic electroluminescence device OLED in which the hole transport region HTR further includes an electron blocking layer EBL disposed between the hole transport layer HTL and the light emitting layer EML.

Figure 5:
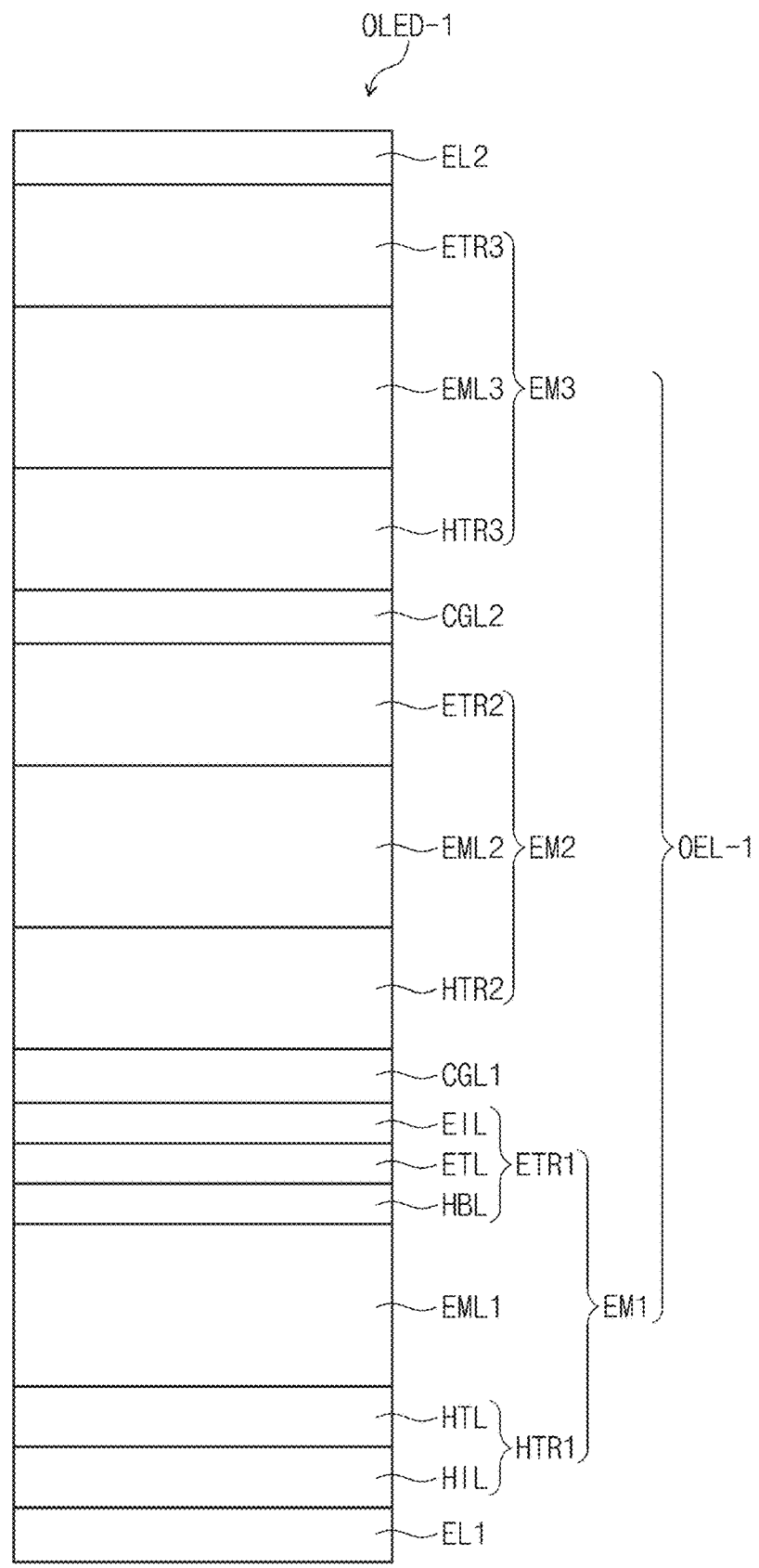
Figure 6:
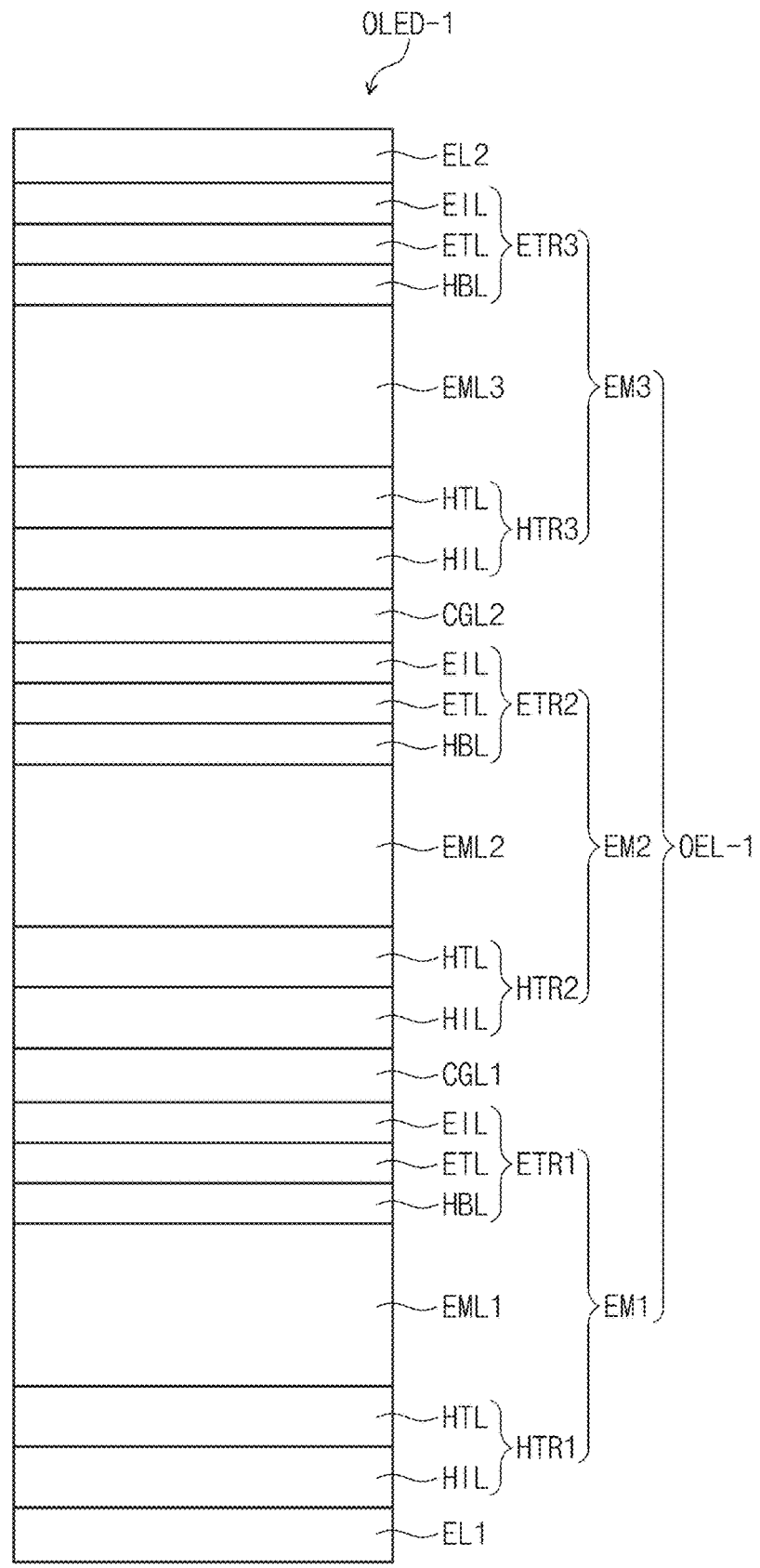

Referring to FIG. 5 and FIG. 6, the organic electroluminescence device OLED-1 may include a first electrode EL1, an organic layer OEL-1, and a second electrode EL2 which are sequentially disposed. The organic electroluminescence device OLED-1 may include a plurality of light emitting units EM1, EM2, and EM3, and a plurality of charge generating layers CGL1 and CGL2 which are disposed between the light emitting units EM1, EM2, and EM3.

A first light emitting unit EM1 may include a first hole transport region HTR1, a first light emitting layer EML1, and a first electron transport region ETR1, which are sequentially disposed. A second light emitting unit EM2 may include a second hole transport region HTR2, a second light emitting layer EML2, and a second electron transport region ETR2, which are sequentially disposed. A third light emitting unit EM3 may include a third hole transport region HTR3, a third light emitting layer EML3, and a third electron transport region ETR3, which are sequentially disposed.

In FIG. 5 and FIG. 6, unless otherwise described, substantially the same contents may be applied to each of the hole transport regions HTR1, HTR2, and HTR3, the light emitting layers EML1, EML2, and EML3, the electron transport regions ETR1, ETR2, and ETR3 as those described above, or to be described, for the hole transport region HTR, the light emitting layer EML, and the electron transport region ETR.

The first hole transport region HTR1 may include the hole injection layer HIL and the electron transport layer ETL which are sequentially disposed, and the first electron transport region ETR1 may include the hole blocking layer HBL, the electron transport layer ETL, and the electron injection layer EIL, which are sequentially disposed. However, the embodiment of the inventive concept is not limited thereto. At least one selected from the first to third hole transport regions HTR1, HTR2, and HTR3 may include the hole injection layer HIL and the electron transport layer ETL, and at least one selected from the first to third electron transport regions ETR1, ETR2, and ETR3 may include the hole blocking layer HBL, the electron transport layer ETL, and the electron injection layer EIL.

For example, as shown in FIG. 6, all of the first to third hole transport regions HTR1, HTR2, and HTR3 may include the hole injection layer HIL and the electron transport layer ETL, and all of the first to third electron transport regions ETR1, ETR2, and ETR3 may include the hole blocking layer HBL, the electron transport layer ETL, and the electron injection layer EIL.

When voltage is applied to each of the charge generating layers CGL1 and CGL2, charges are generated. The charge generating layers CGL1 and CGL2 are disposed between the light emitting units EM1, EM2, and EM3 and control the charge balance between the light emitting units EM1, EM2, and EM3. For example, a first charge generating layer CGL1 may serve to assist the electron injection to the first light emitting unit EM1 and to assist the hole injection to the second light emitting unit EM2.

The charge generating layers CGL1 and CGL2 may be composed of one layer in which an electron injection material and a hole injection material are mixed. Alternatively, the charge generating layers CGL1 and CGL2 may be composed of two or more layers. For example, each of the charge generating layers CGL1 and CGL2 may include an n-type charge generating layer doped with an N-type dopant and a p-type charge generating layer doped with a P-type dopant. The n-type charge generating layer may be a layer disposed directly on or adjacent to the electron transport region ETR to assist the electron injection, and the p-type charge generating layer may be a layer disposed directly on or adjacent to the hole transport region HTR to assist the hole injection.

Materials of the charge generating layers CGL1 and CGL2 are not particularly limited, and any materials known to those skilled in the art may be used without limitation.

Although not illustrated, in the organic electroluminescence device OLED-1 of an embodiment, the charge generating layers CGL1 and CGL2 may be omitted.

The first light emitting layer EML1 may emit a first color light, the second light emitting layer EML2 may emit a second color light, and the third light emitting layer EML3 may emit a third color light. The first to third color light may be the same color light having the same wavelength region or different color light having different wavelength regions. For example, the first to third color light may be blue light having the same wavelength region, specifically, blue light having a wavelength region of 430 nm to 500 nm, or 440 nm to 490 nm. In another example, the first color light may be blue light, the second color light may be green light, and the third color light may be red light. Alternatively, the first to third color light may be blue light having different center wavelength regions. However, the embodiment of the inventive concept is not limited thereto. Each of the light emitting layers EML1, EML2, and EML3 may emit light having various wavelength regions.

Since the plurality of the light emitting layers EML1, EML2, and EML3 are disposed in the organic electroluminescence device OLED-1 of an embodiment, current efficiency may increase and a long life of the device may be achieved.

FIG. 5 and FIG. 6 illustrate three light emitting units. However, the embodiment of the inventive concept is not limited thereto. Another embodiment may include one, two, or four or more light emitting units. Charge generating layers may be disposed between the light emitting units. Therefore, as the number of the light emitting units increases or decreases, the number of charge generating layers may increase or decrease.

The first electrode EL1 is conductive. The first electrode EL1 may be formed of a metal alloy or a conductive compound. The first electrode EL1 may be an anode. The first electrode EL1 may be a transmissive electrode, a transflective electrode, or a reflective electrode. When the first electrode EL1 is a transmissive electrode, the first electrode EL1 may include a transparent metal oxide, for example, indium tin oxide (ITO), indium zinc oxide (IZO), zinc oxide (ZnO), indium tin zinc oxide (ITZO), or the like. When the first electrode EL1 is a transmissive electrode or a transflective electrode, the first electrode EL1 may include Ag, Mg, Cu, Al, Pt, Pd, Au, Ni, Nd, Ir, Cr, Li, Ca, LiF/Ca, LiF/Al, Mo, Ti, or a compound or a mixture thereof (for example, a mixture of Ag and Mg). Alternatively, the first electrode EL1 may be of a multi-layered structure including a reflective film or a transflective film, both formed of the above exemplified materials, and a transparent conductive film formed of indium tin oxide (ITO), indium zinc oxide (IZO), zinc oxide (ZnO), indium tin zinc oxide (ITZO), or the like. For example, the first electrode EL1 may have a three-layered structure of ITO/Ag/ITO, but is not limited thereto. The thickness of the first electrode EL1 may be about 100 Å to about 10000 Å, for example, about 100 Å to about 3000 Å.

The hole transport region HTR is provided on the first electrode EL1. As described above, the hole transport region HTR may include at least one of the hole injection layer HIL, the hole transport layer HTL, a hole buffer layer (not shown), or the electron blocking layer EBL.

The hole transport region HTR may have a single layer structure having a single layer formed of a single material, a single layer structure having a single layer formed of a plurality of different materials, or a multilayer structure having a plurality of layers formed of a plurality of different materials.

For example, the hole transport region HTR may have a single layer structure having a single layer of the hole injection layer HIL or the hole transport layer HTL, or a single layer structure having a single layer formed of a hole injection material and a hole transport material. Also, the hole transport region HTR may have a single layer structure having a single layer formed of a plurality of different materials, or have a structure of hole injection layer HIL/hole transport layer HTL, hole injection layer HIL/hole transport layer HTL/hole buffer layer (not shown), hole injection layer HIL/hole buffer layer (not shown), hole transport layer HTL/hole buffer layer (not shown), or hole injection layer HIL/hole transport layer HTL/electron blocking layer EBL, sequentially disposed on the first electrode ELL but the embodiment of the inventive concept is not limited thereto.

The hole transport region HTR may be formed by various methods such as vacuum deposition, spin coating, casting, Langmuir-Blodgett (LB), inkjet printing, laser printing, and laser induced thermal imaging (LITI).

The hole injection layer HIL may include, for example, a phthalocyanine compound such as copper phthalocyanine; N,N'-diphenyl-N,N-bis-[4-(phenyl-m-tolyl-amino)-phenyl]-biphenyl-4,4'-diamine (DNTPD), 4,4',4"-tris(3-methylphenylphenylamino) triphenylamine (m-MTDATA), 4,4'4"-Tris (N,N-diphenylamino)triphenylamine (TDATA), 4,4',4"-tris{N,-(2-naphthyl)-N-phenylamino}-triphenylamine (2-TNATA), Poly(3,4-ethylenedioxythiophene)/Poly(4-styrenesulfonate) (PEDOT/PSS), Polyaniline/Dodecylbenzenesulfonic acid (PANI/DBSA), Polyaniline/Camphor sulfonic acid PANI/CSA), (Polyaniline)/Poly(4-styrenesulfonate) (PANI/PSS), N,N'-di(naphthalene-1-yl)-N,N-diplienyl-benzidine (NPD), triphenylamine-containing polyether ketone (TPAPEK), 4-Isopropyl-4'-methyldiphenyliodonium Tetrakis(pentafluorophenyl)borate], dipyrazino[2,3-f: 2',3'-h] quinoxaline-2,3,6,7,10,11-hexacarbonitrile (HAT-CN), and the like.

The hole transport layer HTL may further include, for example, a carbazole-based derivative such as N-phenylcarbazole and polyvinylcarbazole, a fluorine-based derivative, a triphenylamine-based derivative such as N,N'-bis(3-methylphenyl)-N,N-diphenyl-[1,1-biphenyl]-4,4'-diamine (TPD) and 4,4',4"-tris(N-carbazolyl)triphenylamine (TCTA), N,N'-di(naphthalene-1-yl)-N,N'-diplienyl-benzidine (NPB), 4,4'-Cyclohexylidene bis[N,N-bis(4-methylphenyl)benzenamine] (TAPC), 4,4'-Bis[N,N'-(3-tolyl)amino]-3,3'-dimethylbiphenyl (HMTPD), (1,3-Bis(N-carbazolyl) benzene (mCP), and the like.

The thickness of the hole transport region HTR may be about 100 Å to about 10000 Å, for example, about 100 Å to about 5000 Å. The thickness of the hole injection layer HIL may be about 30 Å to about 1000 Å, and the thickness of the hole transport layer HTL may be about 30 Å to about 1000 Å. For example, the thickness of the electron blocking layer EBL may be about 10 Å to about 1000 Å. When the thicknesses of the hole transport region HTR, the hole injection layer HIL, the hole transport layer HTL, and the electron blocking layer EBL satisfy the above-described ranges, satisfactory hole transport properties may be obtained without a substantial increase in driving voltage.

The hole transport region HTR may further include a charge generating material to improve conductivity in addition to the above-mentioned materials. The charge generating material may be uniformly or non-uniformly dispersed in the hole transport region HTR. The charge generating material may be, for example, a p-dopant. The p-dopant may be one of a quinone derivative, a metal oxide, or a compound containing a cyano group, but is not limited thereto. For example, non-limiting examples of the p-dopant may include a quinone derivative such as tetracyanoquinodimethane (TCNQ) and 2,3,5,6-tetrafluoro-tetracyanoquinodimethane (F4-TCNQ), and a metal oxide such as a tungsten oxide and a molybdenum oxide, but are not limited thereto.

As described above, the hole transport region HTR may further include at least one of the hole buffer layer (not shown) and the electron blocking layer EBL in addition to the hole injection layer HIL and the hole transport layer HTL. The hole buffer layer (not shown) may increase light emission efficiency by compensating for a resonance distance according to the wavelength of light emitted from the light emitting layer EML. As for materials which may be included in the hole buffer layer, materials which may be included in the hole transport region HTR may be used. The electron blocking layer EBL is a layer serving to prevent electron injection from the electron transporting region ETR to the hole transporting region HTR.

The light emitting layer EML is provided on the hole transport region HTR. The thickness of the light emitting layer EML may be, for example, about 100 Å to about 1000 Å, or about 100 Å to about 300 Å. The light emitting layer EML may have a single layer structure having a single layer formed of a single material, a single layer structure having a single layer formed of a plurality of different materials, or a multilayer structure having a plurality of layers formed of a plurality of different materials.

In the organic electroluminescence devices OLED and OLED-1 of an embodiment, the light emitting layer EML may include an anthracene derivative, a pyrene derivative, a fluoranthene derivative, a chrysene derivative, a dihydrobenz anthracene derivative, or a triphenylene derivative.

In the organic electroluminescence devices OLED and OLED-1 of an embodiment shown in FIG. 3 to FIG. 6, the light emitting layer EML may include a host and a dopant. The host may include the polycyclic compound according to an embodiment to be described later.

The light emitting layer EML may further include a common material known in the art as a host material. For example, the light emitting layer EML may include, as a host material, at least one of Bis[2-(diphenylphosphino)phenyl] ether oxide (DPEPO), 4,4'-Bis(carbazol-9-yl)biphenyl (CBP), 1,3-Bis(carbazol-9-yl)benzene (mCP), 2,8-Bis(diphenylphosphoryl)dibenzo[b,d]furan (PPF), 4,4',4"-Tris (carbazol-9-yl)-triphenylamine (TcTa), or 1,3,5-tris(N-phenylbenzimidazole-2-yl)benzene (TPBi). However, the embodiment of the inventive concept is not limited thereto. For example, tris(8-hydroxyquinolino)aluminum (Alq3), 4,4'-bis(N-carbazolyl)-1,1'-biphenyl (CBP), poly(n-vinylcabazole (PVK), 9,10-di(naphthalene-2-yl)anthracene (ADN), 4,4',4"-Tris(carbazol-9-yl)-triphenylamine (TCTA), 1,3,5-tris(N-phenylbenzimidazole-2-yl)benzene (TPBi), 3-tert-butyl-9,10-di(naphth-2-yl)anthracene (TBADN), distyrylarylene (DSA), 4,4-bis(9-carbazolyl)-2,2'-dimethyl-biphenyl (CDBP), 2-Methyl-9,10-bis(naphthalen-2-yl)anthracene (MADN), bis[2-(diphenylphosphino)phenyl]ether oxide (DPEPO), Hexaphenyl cyclotriphosphazene (CP1), 1,4-Bis (triphenylsilyl)benzene (UGH2), Hexaphenylcyclotrisiloxane (DPSiO3), Octaphenylcyclotetra siloxane (DPSiO4), 2,8-Bis(diphenylphosphoryl)dibenzofuran (PPF), and the like may be used as a host material.

In an embodiment, the light emitting layer EML may include, as a dopant material known in the art, a styryl derivative (for example, 1,4-bis[2-(3-N-ethylcarbazoryl)vinyl] benzene (BCzVB), 4-(di-p-tolylamino)-4'-[(di-p-tolylamino)styryl] stilbene (DPAVB), and N-(4-((E)-2-(6-((E)-4-(diphenylamino)styryl)naphthalen-2-yl)vinyl)phenyl)-N-phenylbenzenamine (N-BDAVBi), perylene and a derivative thereof (for example, 2,5,5,8,11-tetra-t-butylperylene (TBP)), pyrene and a derivative thereof (for example, 1,1-dipyrene, 1,4-dipyrenylbenzene, and 1,4-Bis(N, N-Diphenylamino)pyrene), and the like.

The electron transport region ETR may have a single layer structure having a single layer formed of a single material, a single layer structure having a single layer formed of a plurality of different materials, or a multilayer structure in combination of one or more layers consisting of a plurality of different materials. Alternatively, the electron transport region ETR may have a multilayer structure having a plurality of layers formed of a plurality of different materials.

The thickness of the electron transport region ETR may be, for example, about 1000 Å to about 1500 Å.

The electron transport region ETR may be formed by various methods such as vacuum deposition, spin coating, casting, Langmuir-Blodgett (LB), inkjet printing, laser printing, and laser induced thermal imaging (LITI).

The electron transport region ETR includes the electron transport layer ETL, and the electron transport region ETR may include the polycyclic compound according to an embodiment to be described later. Also, the electron transport region ETR may further include a known electron transport material. For example, the electron transport region ETR may include Alq3(Tris(8-hydroxyquinolinato) aluminum), 1,3,5-tri[(3-pyridyl)-phen-3-yl] benzene, 2,4,6-tris(3'-(pyridin-3-yl)biphenyl-3-yl)-1,3,5-triazine, 2-(4-(N-phenylbenzoimidazolyl-1-ylphenyl)-9,10-dinaphthylanthracene, TPBi(1,3,5-Tri(1-phenyl-1H-benzo[d]imidazol-2-yl)phenyl), BCP(2,9-Dimethyl-4,7-diphenyl-1,10-phenanthroline), Bphen(4,7-Diphenyl-1,10-phenanthroline), TAZ(3-(4-Biphenylyl)-4-phenyl-5-tert-butylphenyl-1,2,4-triazole), NTAZ(4-(Naphthalen-1-yl)-3,5-diphenyl-4H-1,2,4-triazole), tBu-PBD(2-(4-Biphenylyl)-5-(4-tert-butylphenyl)-1,3,4-oxadiazole), BAlq(Bis(2-methyl-8-quinolinolato-N1,O8)-(1,1'-Biphenyl-4-olato) aluminum), Bebq2(berylliumbis(benzoquinolin-10-olate), ADN(9,10-di(naphthalene-2-yl)anthracene), and a compound thereof. The thicknesses of the electron transport layers ETL may be about 100 Å to about 1000 Å, for example, about 150 Å to about 500 Å. When the thicknesses of the electron transport layers ETL satisfy the above-described ranges, satisfactory electron transport properties may be obtained without a substantial increase in driving voltage.

When the electron transport region ETR includes the electron injection layer EIL, the electron transport region ETR may utilize LiF, lithium quinolate (LIQ), $Li_2O$, BaO, NaCl, CsF, a metal in lanthanoides (such as Yb), and/or a metal halide (such as RbCl and/or RbI), but is not limited thereto. The electron injection layer EIL may be composed of a mixture of an electron transport material and an insulating organo metal salt. The organo metal salt may be a material having an energy band gap of about 4 eV or greater. Specifically, for example, the organo metal salt may include metal acetate, metal benzoate, metal acetoacetate, metal acetylacetonate, or metal stearate. The thicknesses of the electron injection layers EIL may be about 1 Å to about 100 Å, or about 3 Å to about 90 Å. When the thicknesses of the electron injection layers EIL satisfy the above-described ranges, satisfactory electron injection properties may be obtained without a substantial increase in driving voltage.

The electron transport region ETR may include the hole blocking layer HBL as described above. The hole blocking layer HBL includes the polycyclic compound of an embodiment to be described later. The hole blocking layer HBL may further include a known hole blocking material. For example, the hole blocking layer HBL may include at least one of BCP (2,9-dimethyl-4,7-diphenyl-1,10-phenanthroline) and Bphen (4,7-diphenyl-1,10-phenanthroline), but is not limited thereto.

In the organic electroluminescence device OLED of an embodiment, the hole blocking layer HBL may include the polycyclic compound of an embodiment, and at least one layer of the light emitting layer EML and the electron transport layer ETL may include the polycyclic compound of an embodiment.

For example, the hole blocking layer HBL and the light emitting layer EML, or the hole blocking layer HBL and the electron transport layer ETL may include the polycyclic compound of an embodiment, and the hole blocking layer HBL, the light emitting layer EML, and the electron transport layer ETL may all include the polycyclic compound of an embodiment. When the light emitting layer EML may include the polycyclic compound of an embodiment as a material of a light emitting layer EML host.

The hole blocking layer HBL may include only the polycyclic compound of an embodiment, and the electron transport layer ETL may include the polycyclic compound of an embodiment, or may further include at least one electron transport material. The light emitting layer EML may include the polycyclic compound of an embodiment as a host material, or may further include at least one host material.

For example, the hole blocking layer HBL may include only the polycyclic compound of an embodiment, and the electron transport layer ETL may include the polycyclic compound of an embodiment and at least one electron transport material.

The polycyclic compound of an embodiment may be represented by Formula 1 below.

[Formula 1]

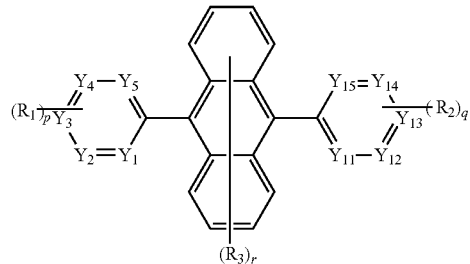

In the present specification, "substituted or unsubstituted" may mean being substituted or unsubstituted with one or more substituents selected from the group consisting of a deuterium atom, a halogen atom, a cyano group, a nitro group, an amino group, a silyl group, an oxy group, a thio group, a sulfinyl group, a sulfonyl group, a carbonyl group, a boron group, a phosphine oxide group, a phosphine sulfide group, an alkyl group, an alkenyl group, an alkoxy group, a hydrocarbon ring group, an aryl group, and a hetero ring group. In addition, each of the substituents illustrated above may be substituted or unsubstituted. For example, a biphenyl group may be interpreted as an aryl group, and may be interpreted as a phenyl group substituted with a phenyl group.

In the present specification, "forms a ring by being coupled to an adjacent group" may mean forming a substituted or unsubstituted hydrocarbon ring or a substituted or unsubstituted hetero ring by being coupled to an adjacent group. The hydrocarbon ring includes an aliphatic hydrocarbon ring and an aromatic hydrocarbon ring. The hetero ring includes an aliphatic hetero ring and an aromatic hetero ring. The hydrocarbon ring and the hetero ring may be monocyclic or polycyclic. Also, a ring formed by being coupled to each other may be connected to another ring to form a spiro structure.

In the present specification, "an adjacent group" may mean a substituent which is substituted with an atom directly connected to an atom with which the substituent is substituted, another substituent substituted with an atom with which the substituent is substituted, or a substituent which is three-dimensional structurally most adjacent to the corresponding substituent. For example, in 1,2-dimethylbenzene, two methyl groups may be interpreted as being "an adjacent group" to each other, and in 1,1-diethylcyclopentene, two ethyl groups may be interpreted as being "an adjacent group" to each other.

In the present specification, the alkyl group may be linear, branched or cyclic. The number of carbon atoms of the alkyl group is 1 to 30, 1 to 20, 1 to 10, or 1 to 6. Examples of the alkyl group may include a methyl group, an ethyl group, an n-propyl group, an isopropyl group, an n-butyl group, an s-butyl group, a t-butyl group, an i-butyl group, a 2-ethylbutyl group, a 3,3-dimethylbutyl group, an n-pentyl group, an i-pentyl group, a neopentyl group, a t-pentyl group, a cyclopentyl group, a 1-methylpentyl group, a 3-methylpentyl group, a 2-ethylpentyl group, a 4-methyl-2-pentyl group, an n-hexyl group, a 1-methylhexyl group, a 2-ethylhexyl group, a 2-butylhexyl group, a cyclohexyl group, a 4-methylcyclohexyl group, a 4-t-butylcyclohexyl group, an n-heptyl group, a 1-methylheptyl group, a 2,2-dimethylheptyl group, a 2-ethylheptyl group, a 2-butylheptyl group, an n-octyl group, a t-octyl group, a 2-ethyloctyl group, a 2-butyloctyl group, a 2-hexyloctyl group, a 3,7-dimethyloctyl group, a cyclooctyl group, an n-nonyl group, an n-decyl group, an adamantly group, a 2-ethyldecyl group, a 2-butyldecyl group, a 2-hexyldecyl group, a 2-octyldecyl group, an n-undecyl group, an n-dodecyl group, a 2-ethyldodecyl group, a 2-butyldodecyl group, a 2-hexyldodecyl group, a 2-octyldodecyl group, an n-tridecyl group, an n-tetradecyl group, an n-pentadecyl group, an n-hexadecyl group, a 2-ethylhexadecyl group, a 2-butylhexadecyl group, a 2-hexylhexadecyl group, a 2-octylhexadecyl group, an n-heptadecyl group, an n-octadecyl group, an n-nonadecyl group, an n-eicosyl group, a 2-ethyleicosyl group, a 2-butyleicosyl group, a 2-hexyleicosyl group, a 2-octyleicosyl group, an n-heneicosyl group, an n-docosyl group, an n-tricosyl group, an n-tetracosyl group, an n-pentacosyl group, an n-hexacosyl group, an n-heptacosyl group, an n-octacosyl group, an n-nonacosyl group, and an n-triacontyl group, and the like, but are not limited thereto.

In the present specification, the hydrocarbon ring group means any functional group or substituent derived from an aliphatic hydrocarbon ring. The hydrocarbon ring group may be a saturated hydrocarbon ring group having a ring-forming carbon atoms of 5 to 20.

In the present specification, the aryl group means any functional group or substituent derived from an aromatic hydrocarbon ring. The aryl group may be a monocyclic aryl group or a polycyclic aryl group. The number of ring-forming carbon atoms of the aryl group may be 6 to 60, 6 to 30, 6 to 20, or 6 to 15. Examples of the aryl group may include a phenyl group, a naphthyl group, a fluorenyl group, an anthracenyl group, a phenanthryl group, a biphenyl group, a terphenyl group, a quaterphenyl group, a quinphenyl group, a sexiphenyl group, a biphenylene group, a triphenylene group, a pyrenyl group, a benzofluoranthenyl group, a chrysenyl group, and the like, but are not limited thereto.

In the present specification, the heteroaryl group may be a heteroaryl group including one or more of B, O, N, P, Si, and S as a hetero atom. When the heteroaryl group includes two or more hetero atoms, the two or more hetero atoms may be the same or different from each other. The heteroaryl group may be a monocyclic heteroaryl group or a polycyclic heteroaryl group. The number of ring-forming carbon atoms of the heteroaryl group may be 2 to 30, 2 to 30, 2 to 20, or 2 to 10. Examples of the heteroaryl group may include a thiophene group, a furan group, a pyrrole group, an imidazole group, a thiazole group, an oxazole group, an oxadiazole group, a triazole group, a pyridine group, a bipyridine group, a pyrimidine group, a triazine group, a triazole group, an acridyl group, a pyridazinyl group, a pyrazinyl group, a quinoline group, a quinazoline group, a quinoxaline group, a phenothiazine group, a phthalazine group, a pyrido pyrimidine group, a pyrido pyrazine group, a pyrazino pyrazine group, an isoquinoline group, an indole group, a carbazol group, an N-arylcarbazol group, an N-heteroarylcarbazole group, an N-alkylcarbazol group, a benzooxazole group, a benzoimidazole group, a benzothiazole group, a benzocarbazole group, a benzothiophene group, a dibenzothiophene group, a thienothiophene group, a benzofuran group, a phenanthroline group, a thiazole group, an isoxazole group, an oxadiazol group, a thiadiazole group, a phenothiazine group, a dibenzosilyl group, a dibenzofuran group, and the like, but are not limited thereto.

In the present specification, the silyl group includes an alkylsilyl group and an arylsilyl group. Examples of the silyl group may include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, and the like, but are not limited thereto.

In the present specification, the boron group includes an alkyl boron group and an aryl boron group. Examples of the boron group may include a trimethylboron group, a triethylboron group, a t-butyldimethylboron group, a triphenylboron group, a diphenylboron group, a phenylboron group, and the like, but are not limited thereto.

In Formula 1, $Y_1$ to $Y_5$ and $Y_{11}$ to $Y_{15}$ may each be independently CH or N. At least four among $Y_1$ to $Y_5$ may be CH, and at least four among $Y_{11}$ to $Y_{15}$ may be CH. That is, each of aromatic hexagonal rings substituted with an anthracene core may be a substituted phenyl group or a substituted pyrimidyl group.

$R_1$ to $R^3$ may each independently be an alkyl group, a silyl group, a boron group, an aryl group, or a heteroaryl group.

The alkyl group may be a substituted or unsubstituted alkyl group having 2 to 20 carbon atoms. The silyl group may be a substituted silyl group, and the boron group may be a substituted boron group. The aryl group may be a substituted or unsubstituted aryl group having 6 to 30 ring-forming carbon atoms. The heteroaryl group may be a substituted or unsubstituted heteroaryl group having 3 to 30 ring-forming carbon atoms, or may form a ring by being coupled to an adjacent group.

When $R_1$ to $R_3$ are substituents having a small volume such as an alkyl group having 1 carbon atom (that is, a methyl group), an unsubstituted silyl group, or an unsubstituted boron group, film formability is poor, so that the formation of a uniform thin film may be difficult. Thus, a driving voltage may be increased.

The polycyclic compound of an embodiment forms a thin film by using materials in which substituents having a relatively large volume such as alkyl groups having 2 or more carbon atoms, a substituted silyl group, or a substituted boron group are substituted. Accordingly, a uniform thin film may be formed, so that a low driving voltage may be implemented.

When each of $R_1$ $R_2$, and $R_3$ is a heteroaryl group, the heteroaryl group may be an electron withdrawing group. For example, the heteroaryl group may be a substituted or unsubstituted pyridine group, a substituted or unsubstituted bipyridine group, a substituted or unsubstituted pyrimidine group, a substituted or unsubstituted triazine group, a substituted or unsubstituted quinoline group, a substituted or unsubstituted quinazoline group, a substituted or unsubstituted quinoxaline group, a substituted or unsubstituted phthalazine group, a substituted or unsubstituted indole group, a substituted or unsubstituted pyrazine group, a substituted or unsubstituted pyridazine group, a substituted or unsubstituted thiophene group, a substituted or unsubstituted oxazole group, a substituted or unsubstituted thiazole group, or a substituted or unsubstituted pyrazole group. In an embodiment, when each of $R_1$, $R_2$, and $R_3$ is an electron withdrawing group, hole blocking properties may be better than when each of $R_1$, $R_2$, and $R_3$ is an electron donating group.

Each of p and q may independently be an integer of 1 to 5. For example, each of p and q may independently be 1 or 2. When p or q is 2 or more, a plurality of substituents may be the same or different from each other.

r may be an integer of 1 to 8. When r is 2 or more, a plurality of substituents may be the same or different from each other.

Formula 1 may be represented by, for example, Formula 2-1 to Formula 2-3 below.

[Formula 2-1]

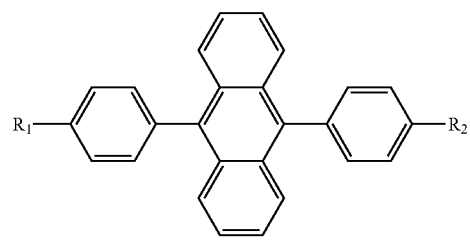

[Formula 2-2]

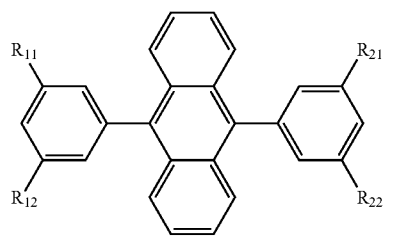

[Formula 2-3]

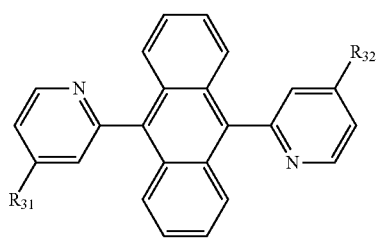

Formula 2-1 to Formula 2-3 are compounds that are specific to the numbers and substitution positions of $R_1$ to $R_2$, and the atoms of $Y_1$ to $Y_5$, and $Y_{11}$ to $Y_{15}$, respectively. $R_1$, $R_2$, $R_{11}$, $R_{14}$, $R_{31}$, and $R_{32}$ may be the same as $R_1$ to $R_3$ defined in Formula 1.

The polycyclic compound of an embodiment may include at least one among the compounds represented by Compound Group 1 below.

[Compound Group 1]

1

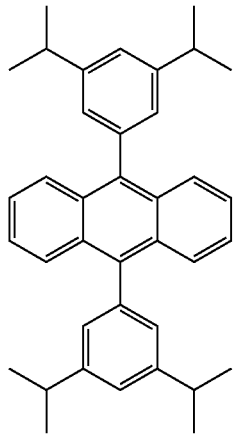

2

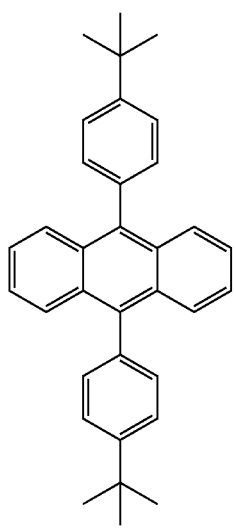

3

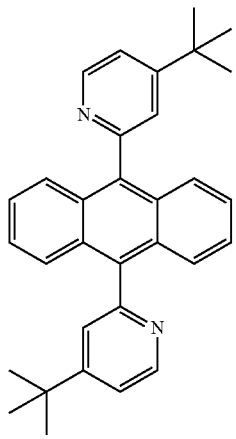

-continued

4

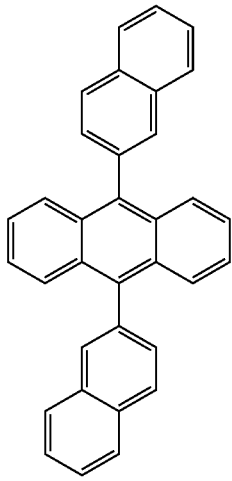

The difference in the highest occupied molecular orbital (HOMO) energy level between the light emitting layer EML host and the polycyclic compound of an embodiment may be 0 eV to 0.1 eV. In an embodiment, when the light emitting layer EML host and the polycyclic compound all have an anthracene core, the HOMO energy level may be similarly formed. Accordingly, remaining holes in the light emitting layer EML may be reduced since remaining holes in the host after the generation of excitons are released. Therefore, the deterioration caused by an exciton-polaron (electron or hole) extinction phenomenon (Triplet-Polaron quenching; TPQ or Singlet-Polaron quenching; SPQ) in the light emitting layer EML may be prevented.

The difference between the lowest occupied molecular orbital (LOMO) energy level of the light emitting layer EML host and the LOMO energy level of the polycyclic compound of an embodiment may be 0 eV to 0.1 eV. Accordingly, due to the small difference in the LUMO energy level between the light emitting layer EML and the hole blocking layer HBL, electrons may be smoothly injected into the light emitting layer EML and light emitting efficiency may be improved. Since the polycyclic compound of an embodiment has substituents having a large volume substituted, the hole mobility of the polycyclic compound may be 0 cm$^2$/Vs to $10^{-6}$ cm$^2$/Vs. Since the polycyclic compound according to an embodiment has a small hole mobility value of $10^{-6}$ cm$^2$/Vs or less, even when the energy difference in each of the HOMO energy level and the LUMO energy level between the polycyclic compound of an embodiment and the light emitting layer EML host material is small, excellent hole blocking properties are exhibited. Particularly, when the polycyclic compound of an embodiment is used as a material for the hole blocking layer HBL, the hole blocking layer HBL may be formed to be thin, so that excellent hole blocking properties may be exhibited while achieving a low driving voltage.

The triplet energy level of the polycyclic compound of an embodiment may be 1.6 eV to 1.8 eV. In the present specification, unless otherwise noted, the triplet energy level may mean the lowest triplet energy level. The difference in triplet energy level between the polycyclic compound and the triplet energy level of the light emitting layer EML host may be small, and the triplet energy level of the polycyclic compound may be smaller than the triplet energy level of the light emitting layer EML host. For example, the difference in triplet energy level between the polycyclic compound and the triplet energy level of the light emitting layer EML host may be about 0 eV to about 0.2 eV. Accordingly, even though some holes are injected into the hole blocking layer HBL, energy generated by Triplet-Triplet Fusion (TTF) in the hole blocking layer HBL may easily move to the light emitting layer EML, so that triple leakage is mitigated to prevent device efficiency from being deteriorated.

Typically, since the triplet energy level difference between the light emitting layer EML host and the hole blocking layer EBL material was designed to be large, an exciton of a long lifespan in a triplet state remained at an interface between the light emitting layer EML and the hole blocking layer HBL, continuously causing damage. In the case of the organic electroluminescence device OLED of an embodiment, the triplet energy level difference of the polycyclic compound of an embodiment which is included in the light emitting layer EML host and the hole blocking layer EBL is designed to be small, so that such damage may be mitigated. Accordingly, a long lifespan of the element may be archived. In addition, the efficiency deterioration caused by the reduction in triplet concentration in the light emitting layer EML may be supplemented by Triplet-Triplet Fusion (TTF) generated in the hole blocking layer HBL.

Meanwhile, the polycyclic compound of an embodiment has excellent durability against holes, so that the deterioration rate is low even in constant contact with the holes. In the organic electroluminescence device OLED of an embodiment, the hole blocking layer HBL includes the polycyclic compound of an embodiment, and at least one layer of the light emitting layer EML and the electron transport layer ETL includes the polycyclic compound of an embodiment, so that durability against holes may be further increased to prevent the deterioration of the device, and thus, a long lifespan of the device may be achieved.

The second electrode EL2 is provided on the electron transport region ETR. The second electrode EL2 may be a common electrode or a cathode. The second electrode EL2 may be a transmissive electrode, a transflective electrode, or a reflective electrode. When the second electrode EL2 is a transmissive electrode, the second electrode EL2 may be formed of a transparent metal oxide, for example, indium tin oxide (ITO), indium zinc oxide (IZO), zinc oxide (ZnO), indium tin zinc oxide (ITZO), or the like.

When the second electrode EL2 is a transflective electrode or a reflective electrode, the second electrode EL2 may include Ag, Mg, Cu, Al, Pt, Pd, Au, Ni, Nd, Ir, Cr, Li, Ca, LiF/Ca, LiF/Al, Mo, Ti, or a compound or a mixture thereof (for example, a mixture of Ag and Mg). Alternatively, the first electrode EL1 may be of a multi-layered structure including a reflective film or a transflective film, both formed of the above exemplified materials, and a transparent conductive film formed of indium tin oxide (ITO), indium zinc oxide (IZO), zinc oxide (ZnO), indium tin zinc oxide (ITZO), or the like.

Although not illustrated, the second electrode EL2 may be connected to an auxiliary electrode. When the second electrode EL2 is connected to the auxiliary electrode, the resistance of the second electrode EL2 may be reduced.

Meanwhile, although not shown in the figures, on the second electrode EL2 of the organic electroluminescence device OLED of an embodiment, the capping layer (not shown) may be further disposed. The capping layer (not shown) may include, for example, α-NPD, NPB, TPD, m-MTDATA, Alq3, CuPc, TPD15(N4,N4,N4',N4'-tetra (biphenyl-4-yl) biphenyl-4,4'-diamine), TCTA(4,4',4"-Tris (carbazol sol-9-yl) triphenylamine), N, N'-bis (naphthalen-1-yl), and the like.

FIG. 7 to FIG. 10 are cross-sectional views of display devices DD-1, DD-2, DD-3, and DD-4 according to an embodiment of the inventive concept. The display devices DD-1, DD-2, DD-3, and DD-4 of FIG. 7 to FIG. 10 may have a configuration corresponding to the cross-section of the display device DD shown in FIG. 2.

Figure 7:
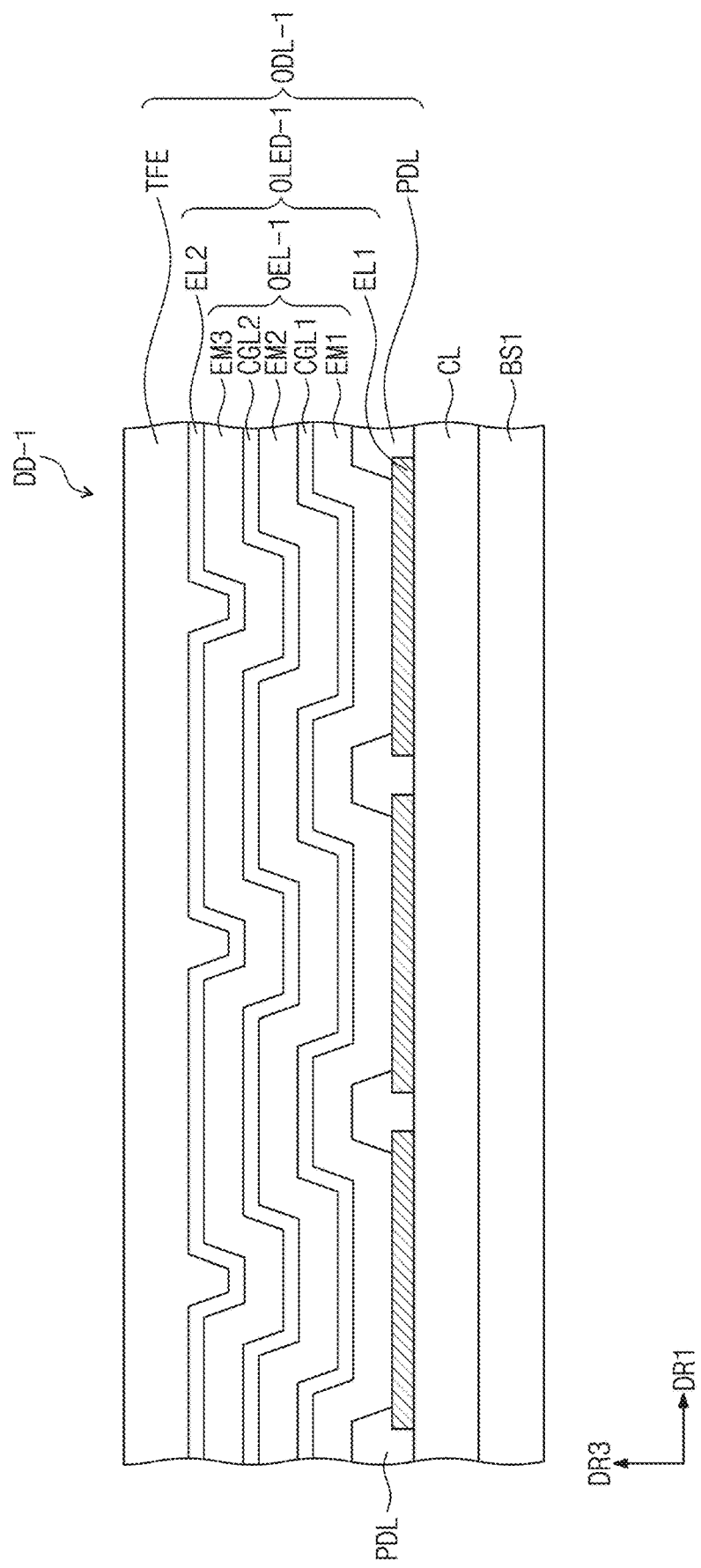
FIG. 7, FIG. 8, FIG. 9, and FIG. 10 are cross-sectional views according to an embodiment of the inventive concept.

Referring to FIG. 7, a display device DD-1 of an embodiment includes an organic electroluminescence device OLED-1. The organic electroluminescence device OLED-1 includes a first electrode EL1, organic layers OEL-1, and a second electrode EL2. The organic electroluminescence device OLED-1 may include a plurality of light emitting units EM1, EM2, and EM3, and charge generating layers CGL1 and CGL2 which are disposed between the light emitting units EM1, EM2, and EM3. In FIG. 7, unless otherwise noted, substantially the same contents may be applied to components corresponding to the components of FIG. 2, FIG. 5, and FIG. 6 as those described above with reference to FIG. 2, FIG. 5, and FIG. 6, and thus a detailed description thereof will be omitted.

Figure 8:
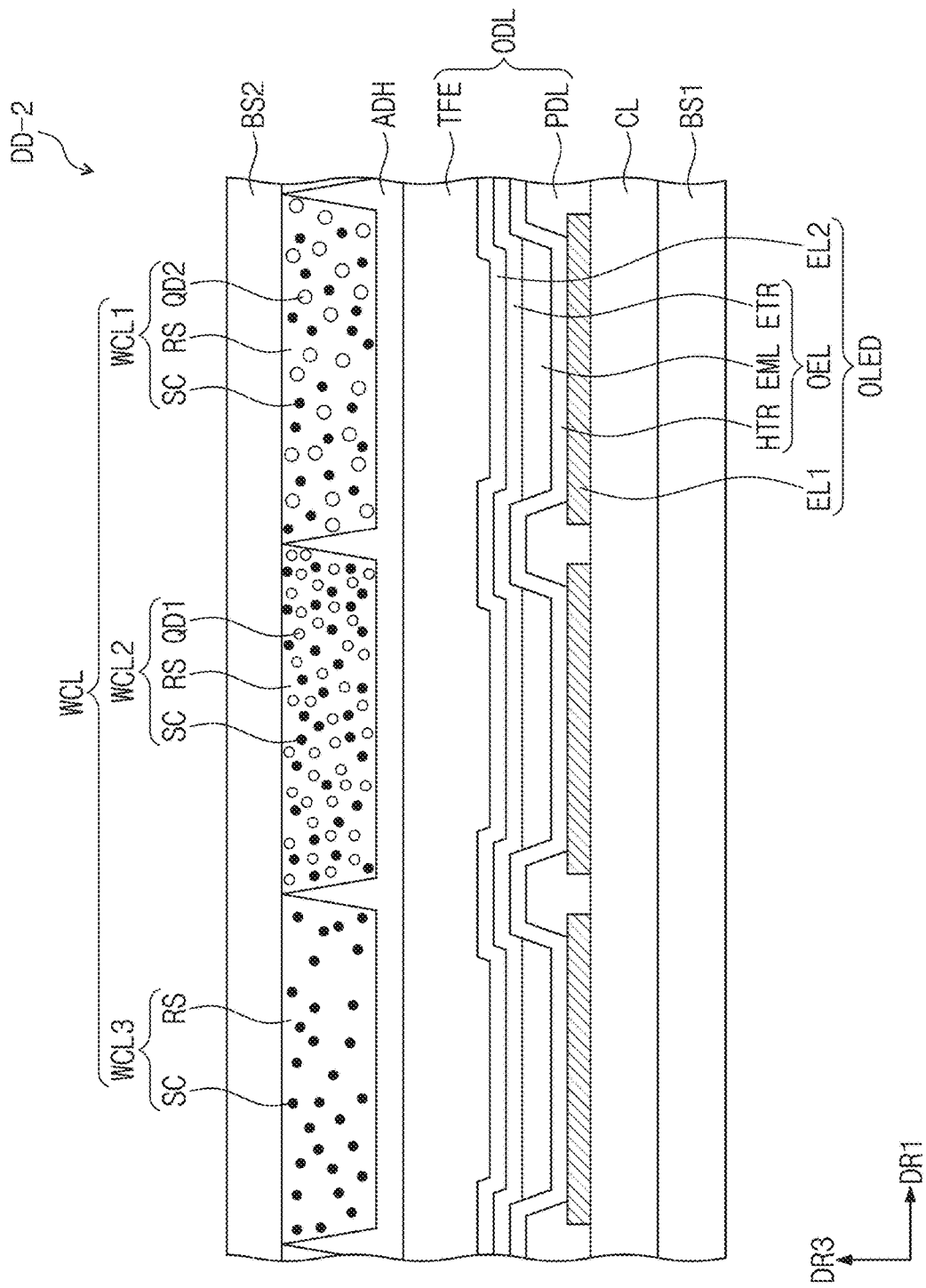

Referring to FIG. 8, a display device DD-2 of an embodiment may include a first base substrate BS1, a circuit layer CL, a light emitting element layer ODL, an adhesive member ADH, a light conversion layer WCL, and a second base substrate BS2. Unless otherwise noted, substantially the same contents may be applied to the first base substrate BS1, the circuit layer CL, and the light emitting element layer ODL as those described above. Although not illustrated, the light emitting element layer ODL may include organic electroluminescence devices including a plurality of light emitting units.

The adhesive member ADH may bond the light emitting element layer ODL and the light conversion layer WCL. The adhesive member ADH may be an optically clear adhesive.

On the adhesive member ADH, the second base substrate BS2 may be disposed. The second base substrate BS2 may be a silicon substrate, a plastic substrate, a glass substrate, an insulation film, or a disposed structural body including a plurality of insulation layers.

Between the adhesive member ADH and the second base substrate BS2, the light conversion layer WCL may be disposed. The light conversion layer WCL may include a first light conversion part WCL1, a second light conversion part WCL2, and a third light conversion part WCL3. The light conversion layer WCL may transmit or absorb a first color light emitted from the light emitting element layer ODL to emit a second color light, or may absorb the first color light color to emit a third color light. Specifically, the first light conversion part WCL1 absorbs the first color light to emit the second color light, the second light conversion part WCL2 absorbs the first color light to emit the third color light, and the third light conversion part WCL3 may transmit the first color light. The first color light may be blue light, the second color light may be green light, and the third color light may be red light.

Each of the first to third light conversion parts WCL1, WCL2, and WCL3 may overlap the light emitting layer EML on a plane, and may overlap a portion of the pixel definition film PDL.

The first light conversion part WCL1 may include a base resin RS, scattering particles SC dispersed in the base resin RS, and a first quantum dot light emitting body QD1. The first quantum dot light emitting body QD1 may absorb the first color light to emit the second color light.

The second light conversion part WCL2 may include the base resin RS, the scattering particles SC dispersed in the base resin RS, and a second quantum dot light emitting body QD2. The second quantum dot light emitting body QD2 may absorb the first color light to emit the third color light.

The third light conversion part WCL3 may include the base resin RS and the scattering particles SC dispersed in the base resin RS. The scattering particles SC may be $TiO_2$ or silica-based nanoparticles. The scattering particles SC may scatter light. Since the third light conversion part WCL3 does not include a quantum dot light emitting body, the amount of the scattering particles SC per unit area included in the third light conversion part WCL may be greater than the amount of the scattering particles SC per unit area included in each of the first light conversion part WCL1 and the second light conversion part WCL2.

Each of the quantum dot light emitting bodies QD1 and QD2 may include a material selected from a Group II-VI compound, a Group III-V compound, a Group IV-VI compound, a Group IV element, a Group IV compound, and a combination thereof. Each of the quantum dot light emitting bodies QD1 and QD2 may be a binary compound, a ternary compound, or a quaternary compound, and may be present in a particle with a uniform concentration distribution, or may be present in the same particle with a partially different concentration. Each of the quantum dot light emitting bodies QD1 and QD2 may have a core-shell structure including a core and a shell surrounding the core. In addition, each of the quantum dot light emitting bodies QD1 and QD2 may have a core-shell structure in which one quantum dot light emitting body surrounds another quantum dot light emitting body. An interface between the core and the shell may have a concentration gradient in which the concentration of an element present in the shell is reduced toward the center.

Each of the quantum dot light emitting bodies QD1 and QD2 may be a particle having a size of nanometers. Each of the quantum dot light emitting bodies QD1 and QD2 may have a full width of half maximum (FWHM) of a light emission wavelength spectrum of about 45 nm or less, preferably about 40 nm or less, more preferably about 30 nm or less, and color purity or color reproducibility may be improved in the above range. In addition, light emitted through such quantum dot light emitting bodies QD1 and QD2 is emitted in all directions, so that a wide viewing angle may be improved.

In addition, although the form of each of the quantum dot light emitting bodies QD1 and QD2 is not particularly limited as long as it is a form commonly used in the art, more specifically, a quantum dot light emitting body in the form of spherical, pyramidal, multi-arm, or cubic nanoparticles, nanotubes, nanowires, nanofibers, nanoparticles, and the like may be used.

Figure 9:
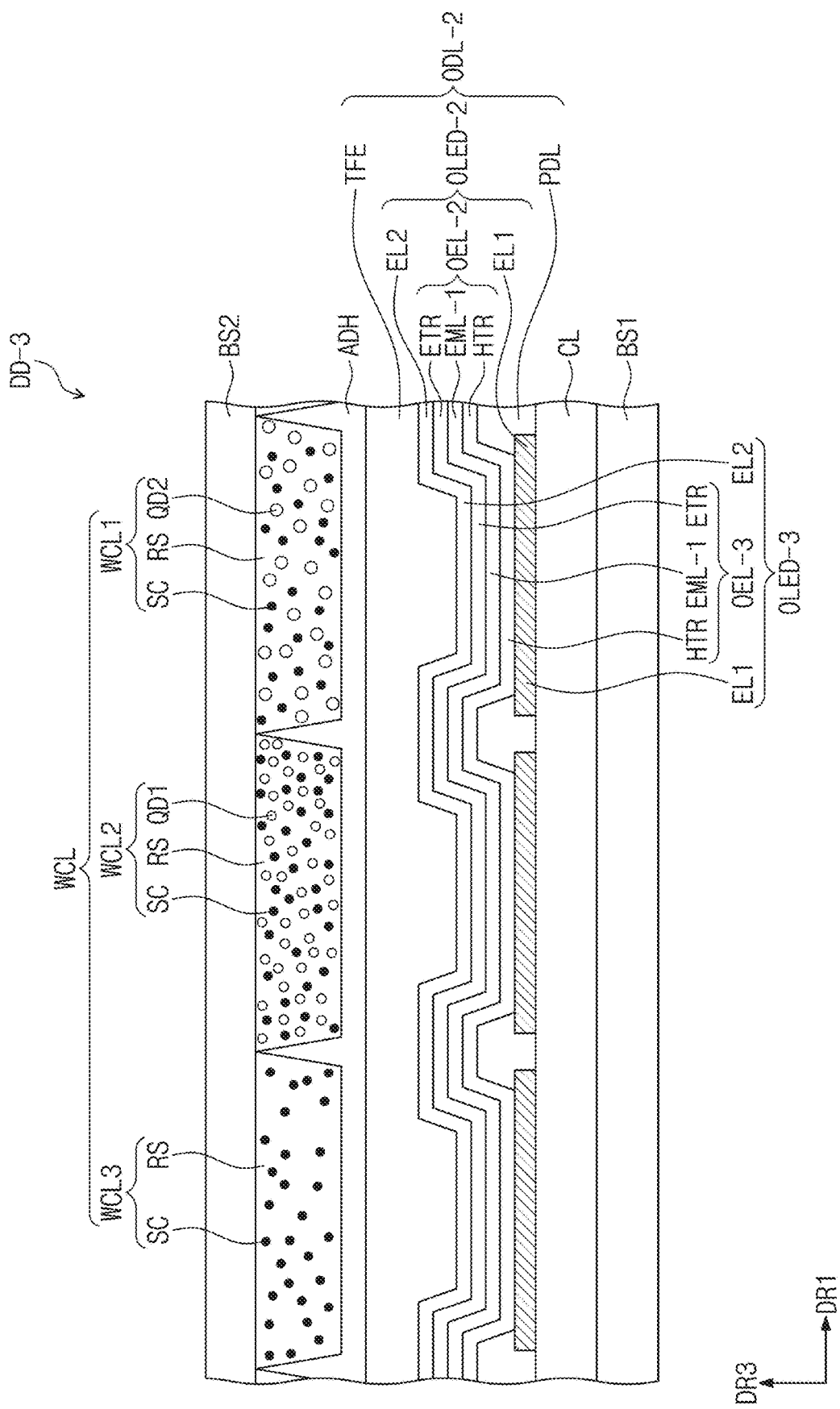

Referring to FIG. 9, in a light emitting element layer ODL-2, a light emitting element layer EML may be disposed as a common layer, that is, one layer, in an organic electroluminescent devices OLED. At this time, since a separate mask for depositing a light emitting layer EML-1 is not required, the manufacturing process of a display device DE-3 may be simplified.

Figure 10:
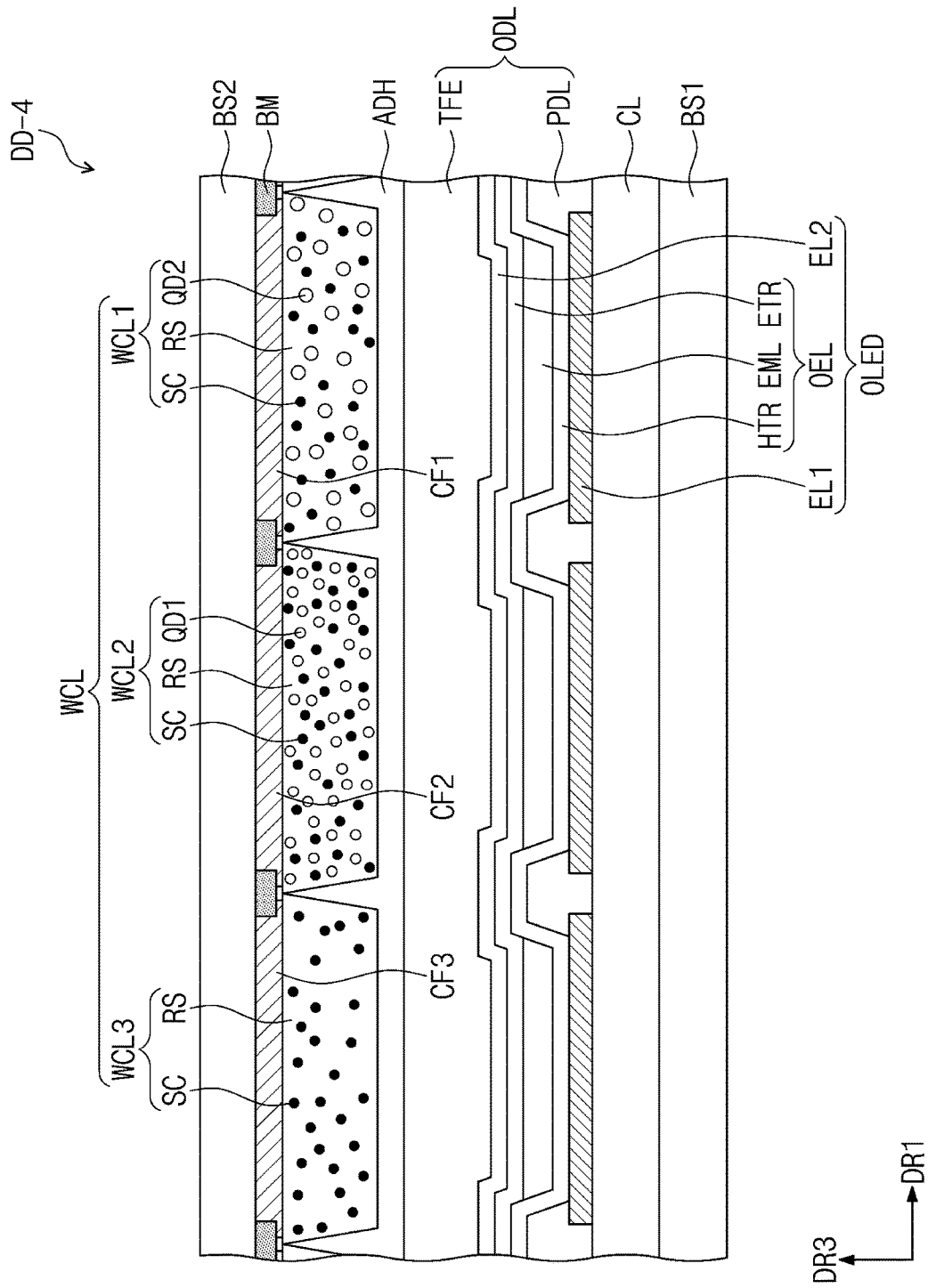

Referring to FIG. 10, a display device DD-4 may include first to third color filters CF1, CF2, and CF3. The first color filter CF1 is disposed on the first light conversion part WCL1 and may overlap the first light conversion part WCL1 on a plane. The second color filter CF2 is disposed on the second light conversion part WCL2 and may overlap the second light conversion part WCL2 on a plane. The third color filter CF3 is disposed on the third light conversion part WCL3 and may overlap the third light conversion part WCL3 on a plane.

Each of the first to third color filters CF1, CF2, and CF3 may transmit light of different wavelengths. For example, the first color filter CF1 may transmit the second color light and absorb other light. The second color filter CF2 may transmit the third color light and absorb other light. The third color filter CF3 may transmit the first color light and absorb other light.

Each of the first to third color filters CF1, CF2, and CF3 may transmit color light corresponding to light emitted from the first to third light conversion layers WCL1, WCL2, and WCL3, and absorb other light. The first color filter CF1 may be a green color filter for transmitting green light. The second color filter CF2 may be a red color filter for transmitting red light. The third color filter CF3 may be a blue color filter for transmitting blue light.

Each of the first to third color filters CF1, CF2, and CF3 includes a base resin, and may include at least one pigment or one dye dispersed in the base resin. Each of the first to third color filters CF1, CF2, and CF3 includes a base resin, and may include at least one dye or pigment dispersed in the base resin. For example, the first color filter CF1 may include at least one green dye or green pigment. The second color filter CF2 may include at least one red dye or red pigment. The third color filter CF3 may include at least one blue dye or blue pigment.

With the first to third color filters CF1, CF2, and CF3 disposed, only the light of a target wavelength region is emitted, so that the color reproducibility of the display device DD-4 may be increased. Also, since light incident from the outside is absorbed to reduce external light reflection, the visibility of the display device DD-4 may be improved.

Between each of the first to third color filters CF1, CF2, and CF3, a light blocking layer BM may be disposed. The light blocking layer BM may be directly disposed under a second base layer. The light blocking layer BM may overlap a non-light emitting region NPXA on a plane. The light blocking layer BM may include carbon black particles. With the light blocking layer BM disposed, light emitted from adjacent pixel regions may be prevented from mixing with each other. In an embodiment, the light blocking layer BM may be omitted.

Hereinafter, with reference to FIG. 11A to FIG. 12B, specific examples, and comparative examples, the inventive concept will be described in more detail.

Figure 11A:
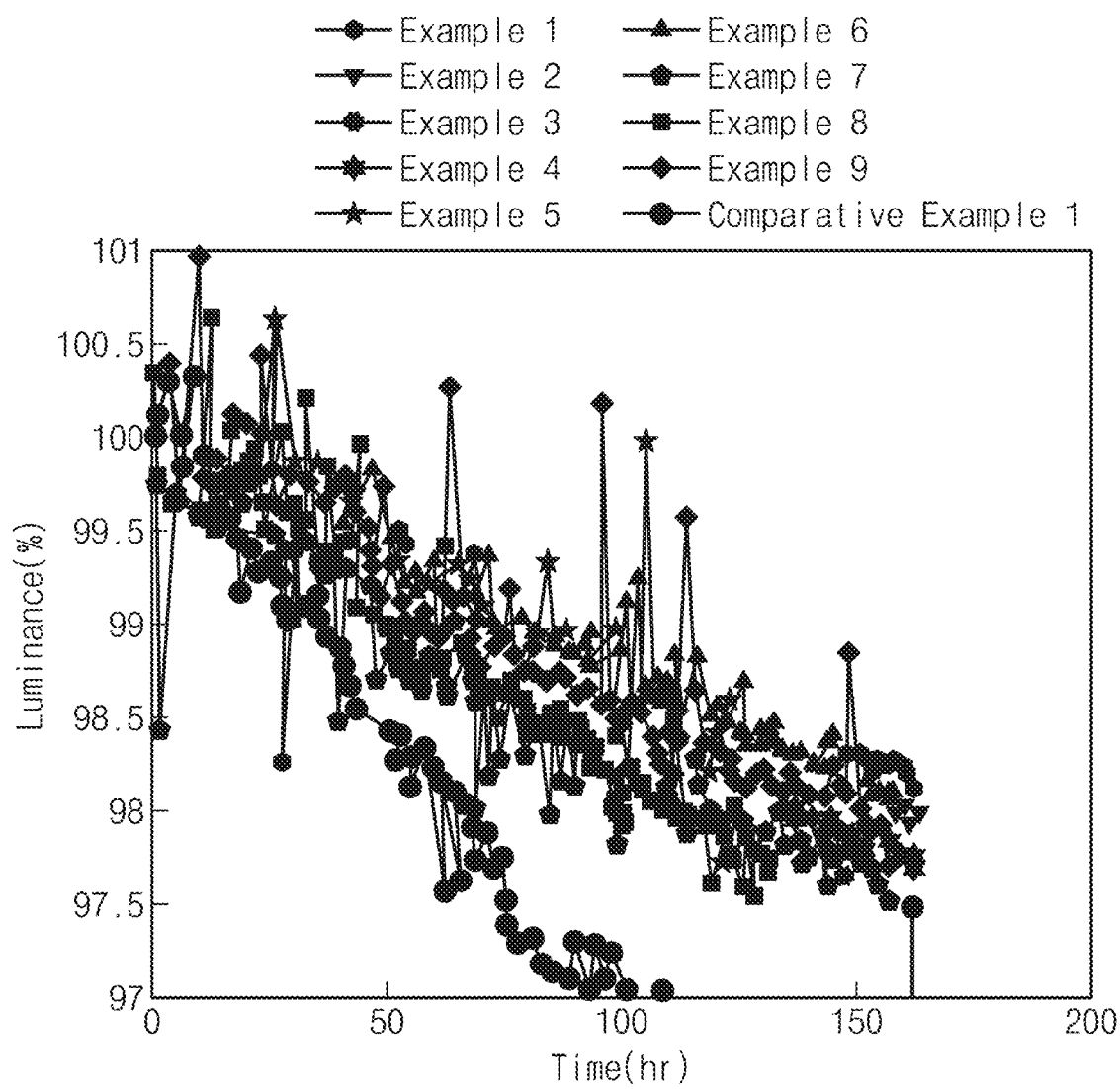
FIG. 11A is a graph showing the luminance reduction amount over time in Examples and Comparative Examples.
Figure 11B:
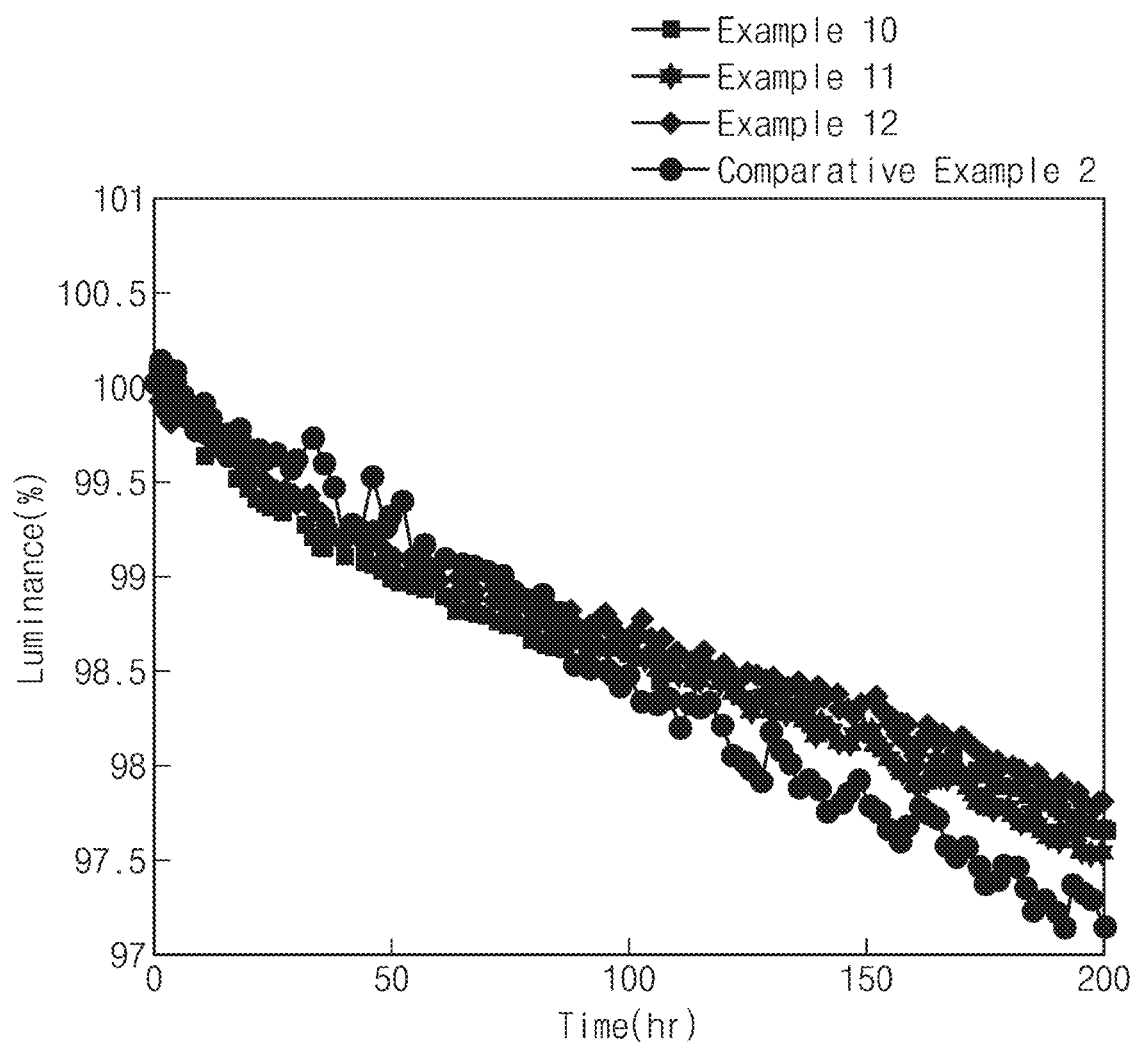
FIG. 11B is a graph showing luminance reduction amount of over time in Examples and Comparative Examples.
Figure 12A:
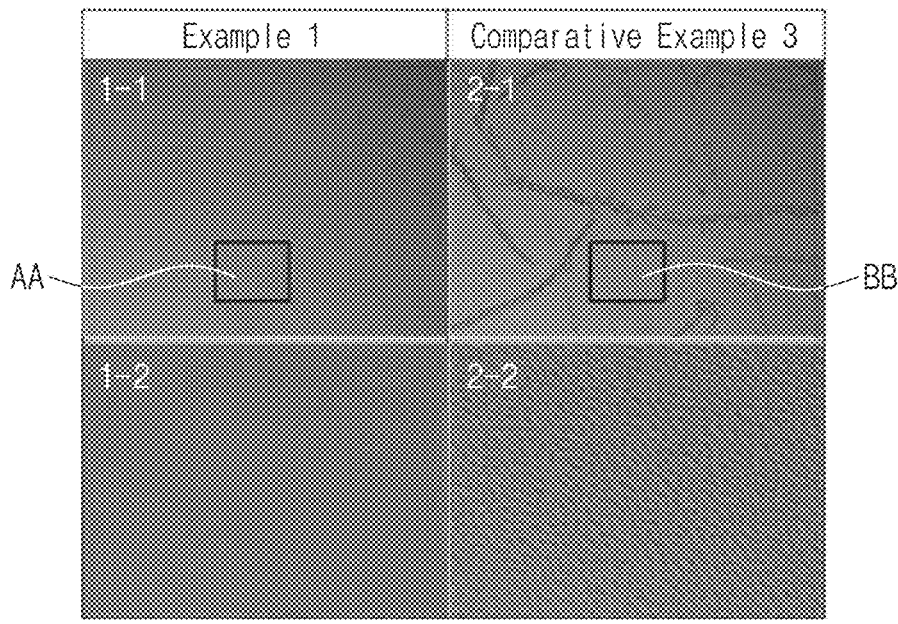
FIG. 12A shows enlarged images of thin films formed according to Examples and Comparative Examples.
Figure 12B:
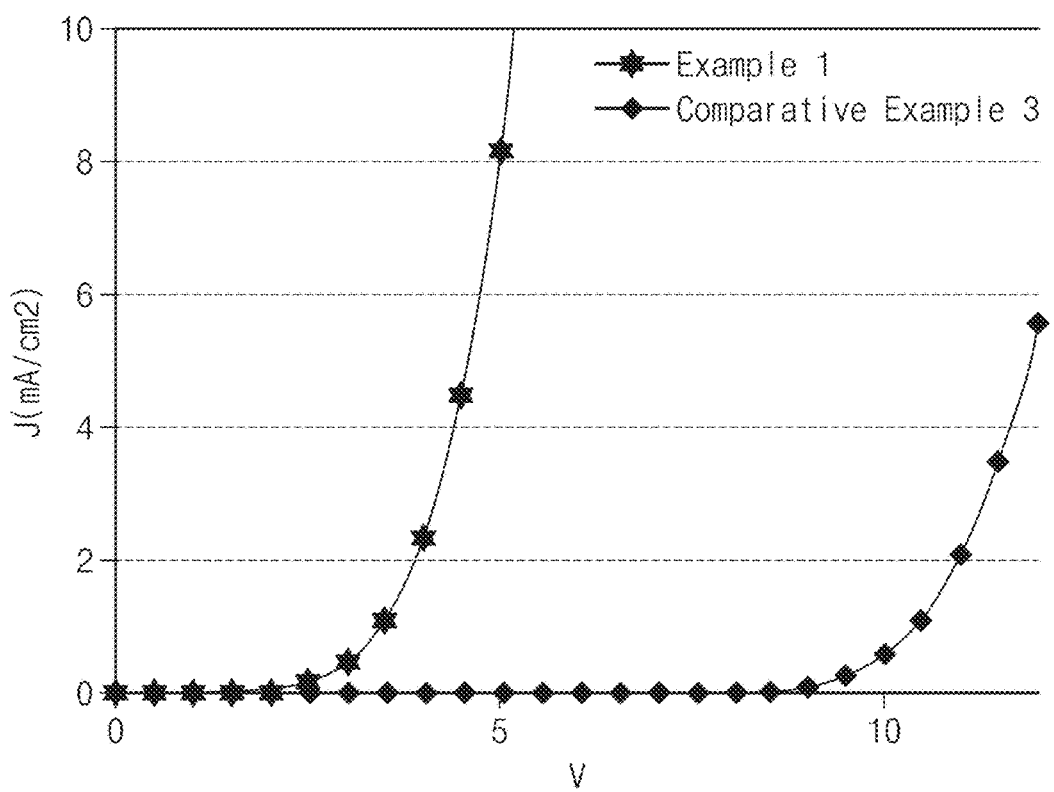
FIG. 12B is a graph showing a current density value according to a drive voltage in Examples and Comparative Examples.

FIG. 11A is a graph showing the luminance reduction amount over time in Examples and Comparative Examples. FIG. 11B is a graph showing the luminance reduction amount over time in Examples and Comparative Examples. FIG. 12A shows enlarged images of thin films formed according to Examples and Comparative Examples. FIG. 12B is a graph showing a current density value according to a drive voltage in Examples and Comparative Examples.

The following examples are for illustrative purposes only to facilitate the understanding of the inventive concept, and thus, the scope of the inventive concept is not limited thereto.

1. Synthesis Example

A polycyclic compound of an embodiment may be synthesized, for example, as follows. However, the synthesis method of the polycyclic compound of an embodiment is not limited thereto.

1-1 Synthesis of Compound 1

The polycyclic compound of an embodiment may be synthesized, for example, by Reaction Formula 1 below.

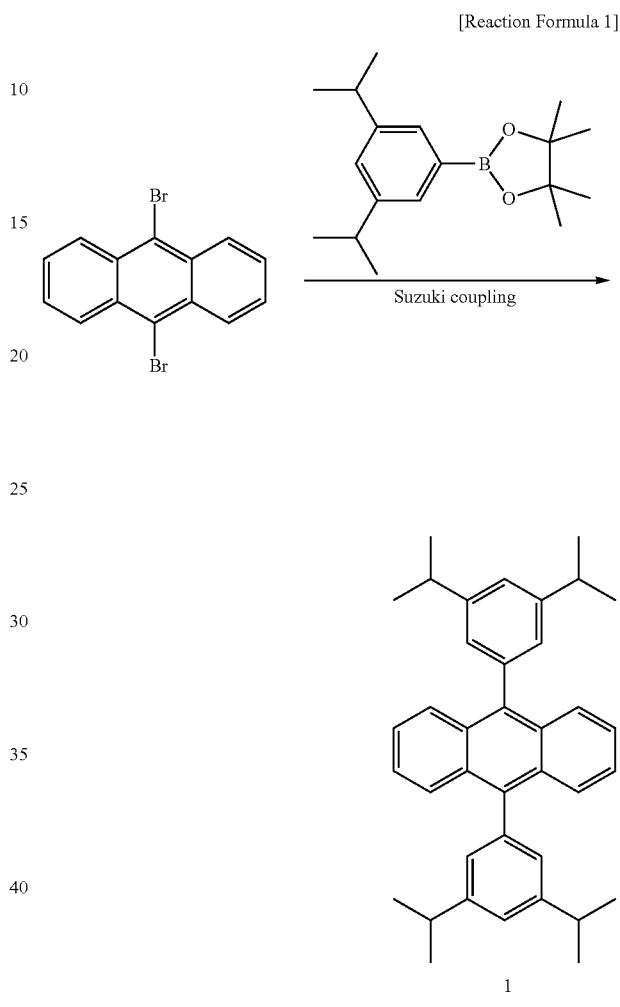

[Reaction Formula 1]

3 g (0.0089 mol) of 9,10-dibromoanthracene and 5.38 g (0.01869 mol) of 2-(3,5-diisopropylphenyl)-4,4,5,5-tetramethyl-1,3,2-dioxaborolane were put into a 3-neck flask (100 ml), added with 3 ml of 2N $Na_2CO_3$ and a mixed solution of Toluene/Ethanol, and then stirred to remove oxygen. Thereafter, in a nitrogen atmosphere, 0.1 g $Pd(pph_3)_4$ was added thereto as a catalyst, and then the mixture was refluxed at 110° C. for 8 hours. The reaction was terminated using water, and an extraction of reactant product was performed three times using methylene chloride ($CH_2Cl_2$). And a solvent was removed. A resultant product obtained therefrom was subjected to column chromatography using a mixed solvent in which ethyl acetate and hexane are mixed at a ratio of 1:10, and 3.91 g (yield 88%) of Compound 1 was obtained. $^1H$ NMR ($CDCl_3$) measurement results of Compound 81 were as follows.

δ 8.23 (4H, d), δ 7.80 (4H, s), δ 7.50 (2H, s), δ 7.37-7.35 (4H, d), δ 2.87 (4H, m), δ 1.30-1.28 (24H, t). 1-2 Synthesis of Compound 2

[Reaction Formula 2]

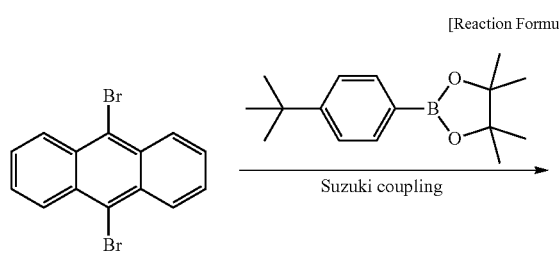

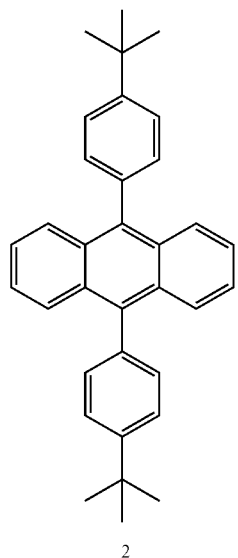

2

3 g (0.0089 mol) of 9,10-dibromoanthracene and 4.86 g (0.01869 mol) of 2-(4-(tert-butyl)phenyl)-4,4,5,5-tetramethyl-1,3,2-dioxaborolane were put into a 3-neck flask (100 ml), added with 3 ml of 2N $Na_2CO_3$ and a mixed solution of Toluene/Ethanol, and then stirred to remove oxygen. Thereafter, in a nitrogen atmosphere, 0.1 g $Pd(pph_3)_4$ was added thereto as a catalyst, and then the mixture was refluxed at 110° C. for 8 hours. The reaction was terminated using water, and an extraction of reactant product was performed three times using methylene chloride ($CH_2Cl_2$). A solvent was removed. A resultant product obtained therefrom was subjected to column chromatography using a mixed solvent in which ethyl acetate and hexane are mixed at a ratio of 1:10, and 3.91 g (yield 88%) of Compound 1 was obtained. $^1$H NMR ($CDCl_3$) measurement results of Compound 81 were as follows.

δ 8.21 (4H, d), δ 7.40-7.30 (12H, m), δ 1.30-1.28 (18H, t).

1-3 Synthesis of Compound 3

[Reaction Formula 3]

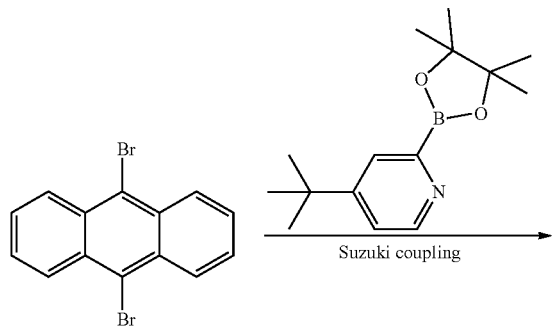

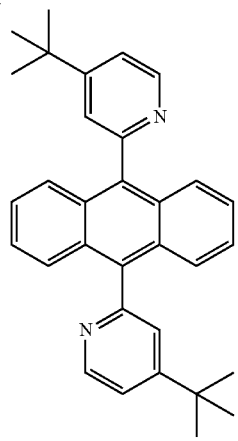

3 g (0.0089 mol) of 9,10-dibromoanthracene and 4.88 g (0.01869 mol) of 4-(tert-butyl)-2-(4,4,5,5-tetramethyl-1,3,2-dioxaborolan-2-yl)pyridine were put into a 3-neck flask (100 ml), added with 3 ml of 2N $Na_2CO_3$ and a mixed solution of Toluene/Ethanol, and then stirred to remove oxygen. Thereafter, in a nitrogen atmosphere, 0.1 g $Pd(pph_3)_4$ was added thereto as a catalyst, and then the mixture was refluxed at 110° C. for 8 hours. The reaction was terminated using water, and an extraction of reactant product was performed three times using methylene chloride ($CH_2Cl_2$). And a solvent was removed. A resultant product obtained therefrom was subjected to column chromatography using a mixed solvent in which ethyl acetate and hexane are mixed at a ratio of 1:10, and 2.97 g (yield 75%) of Compound 3 was obtained. $^1$H NMR ($CDCl_3$) measurement results were as follows.

δ 8.36 (2H, d), δ 8.20 (4H, d), δ 7.80 (2H, s), δ 7.40 (4H, m), δ 7.02 (2H, d), δ 1.30-1.28 (18H, s).

1-4 Synthesis of Compound 4

[Reaction Formula 4]

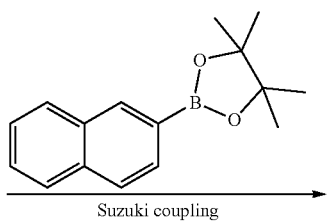

Example Compounds

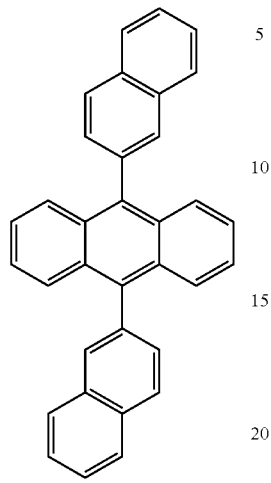

5

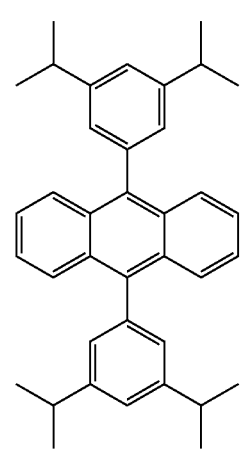

1

3 g (0.0089 mol) of 9,10-dibromoanthracene and 4.75 g (0.01869 mol) of 4,4,5,5-tetramethyl-2-(naphthalen-2-yl)-1,3,2-dioxaborolane were put into a 3-neck flask (100 ml), added with 3 ml of 2N Na₂CO₃ and a mixed solution of Toluene/Ethanol, and then stirred to remove oxygen. Thereafter, in a nitrogen atmosphere, 0.1 g Pd(pph₃)₄ was added thereto as a catalyst, and then the mixture was refluxed at 110° C. for 8 hours. The reaction was terminated using water, and an extraction of reactant product was performed three times using methylene chloride (CH₂Cl₂). A solvent was removed. A resultant product obtained therefrom was subjected to column chromatography using a mixed solvent in which ethyl acetate and hexane are mixed at a ratio of 1:10, and 3.64 g (yield 95%) of Compound 4 was obtained. $^1$H NMR (CDCl₃) measurement results of Compound 81 were as follows.

δ 8.21 (4H, d), δ 8.08-7.95 (6H, m), δ 7.66-7.55 (6H, m), δ 7.40-7.37 (6H, m)

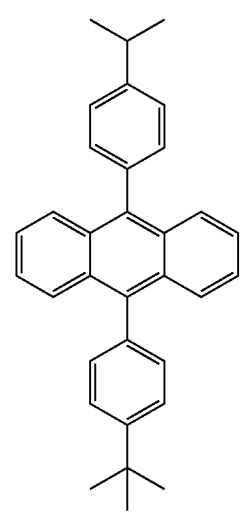

2

2. Manufacturing and Evaluation of Polycyclic Compound and Organic Electroluminescence Device Including Polycyclic Compound 2-1. Energy Level of Polycyclic Compound The HOMO energy level, LUMO energy level, T1 energy level, and S1 energy level of Example Compound 1 to 4 and Comparative Example Compounds X1, X2, and X3 were measured by a nonempirical molecular orbital method. Specifically, using Gaussian09, a product of Gaussian Co., the calculation was performed using B3LYP for a general function and 6-31G(d) for a base function.

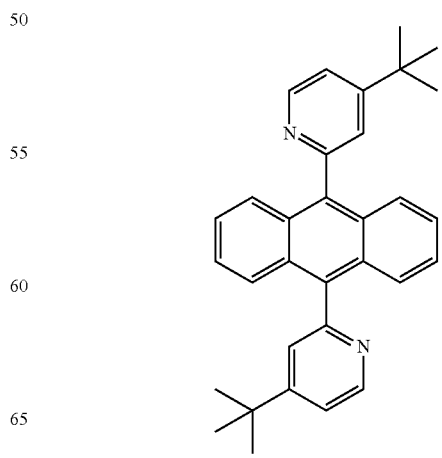

3

Comparative Example Compounds

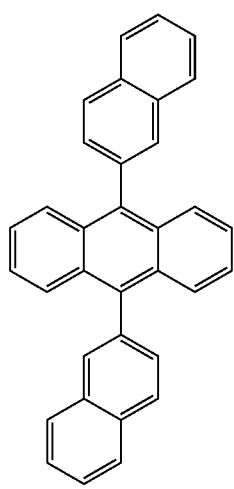

X1

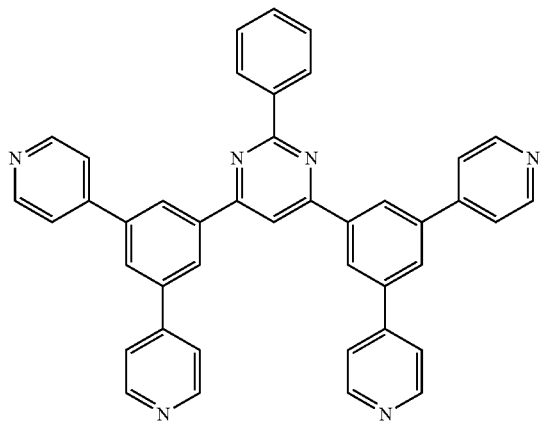

X2

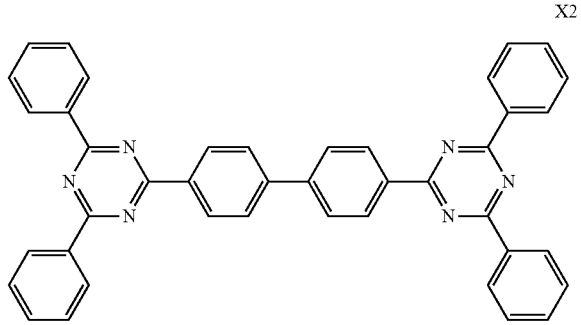

X3

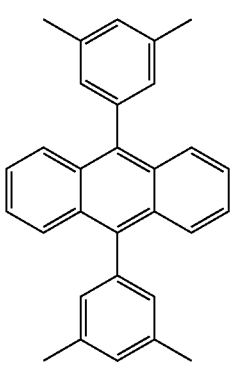

TABLE 1

| Compound | HOMO(eV) | LUMO(eV) | T1(eV) | S1(eV) |
|---|---|---|---|---|
| Example compound 1 | −5.61 | −2.49 | 1.665 | 3.1 |
| Example compound 2 | −5.63 | −2.51 | 1.67 | 3.1 |
| Example compound 3 | −5.58 | −2.53 | 1.75 | 3.1 |
| Example compound 4 | −5.6 | −2.49 | 1.77 | 3.07 |
| Comparative Example compound X1 | −6.05 | −2.58 | 2.7 | 3.2 |
| Comparative Example compound X2 | −5.91 | −2.70 | 2.8 | 3.3 |

The HOMO energy level, LUMO energy level, TI energy level, and Si energy level of Example Compounds 1 to 4 and Comparative Example Compounds X1 and X2 are shown in Table 1.

2-2 Manufacturing of Properties Evaluation of Organic Electroluminescence Device (Manufacturing of Organic Electroluminescence Device)

In the organic electroluminescence devices of Examples 1 to 3 and Comparative Example 1, a first electrode EL1 having a thickness of 30 nm was formed using ITO. A hole injection layer HIL having a thickness of 10 nm was formed of HAT-CN, and a hole transport layer HTL having a thickness of 60 nm was formed using TCTA. In Example Compound 4, a light emitting layer EML doped with 3% of TBP and having a thickness of 20 nm was formed.

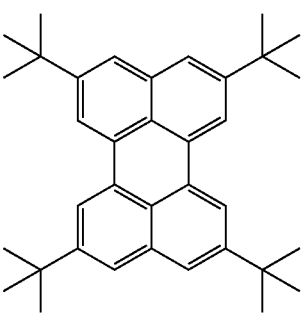

TBP

Thereafter, an electron injection layer EIL having a thickness of 1 nm was formed using Liq. A second electrode EL2 having a thickness of 100 nm was formed using Al. Each layer was formed by vacuum deposition.

In each of Examples 1 to 3, a hole blocking layer HBL having a thickness of 5 nm was formed using Example Compounds 1 to 3, respectively, and an electron transport layer ETL having a thickness of 30 nm was formed by mixing each of Example Compounds 1 to 3 and Liq at a ratio of 1:1.

In each of Examples 7 to 9, a device was manufactured in the same manner as in Examples 1 to 3 except that the electron transport layer ETL was formed using Comparative Example Compound X2 instead of Example Compounds 1 to 3.

In Comparative Example 1, a device was manufactured in the same manner as in Example 1 except that the hole blocking layer HBL was formed using Comparative Example Compound X1 instead of Example Compound 1 and the electron transport layer ETL was formed using Comparative Example X2 instead of Example compound 1.

The material compositions of the light emitting layer, the hole blocking layer, and the electron transport layer of each of Examples 1 to 9 and Comparative Example 1 are shown in Table 2.

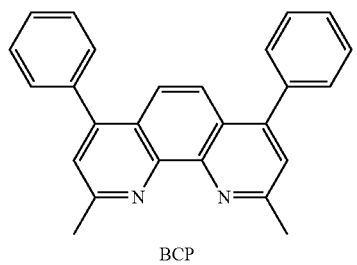

BCP

Thereafter, a hole injection layer HIL having a thickness of 10 nm was formed of NPB, and a hole transport layer HTL having a thickness of 20 nm was formed using TCTA. In Example Compound 4, a second light emitting layer EML2 doped with 3% of TBP below and having a thickness of 20 nm was formed.

TABLE 2

| Manufacturing example of device | Light emitting layer host | Hole blocking layer | Electron transport layer (mixed with Liq at 1:1) |
| --- | --- | --- | --- |
| Example 1 | Example compound 4 | Example compound 1 | Example compound 1 |
| Example 2 | Example compound 4 | Example compound 2 | Example compound 2 |
| Example 3 | Example compound 4 | Example compound 3 | Example compound 3 |
| Example 4 | Example compound 4 | Comparative Example compound X1 | Example compound 1 |
| Example 5 | Example compound 4 | Comparative Example compound X1 | Example compound 2 |
| Example 6 | Example compound 4 | Comparative Example compound X1 | Example compound 3 |
| Example 7 | Example compound 4 | Example compound 1 | Comparative Example compound X2 |
| Example 8 | Example compound 4 | Example compound 2 | Comparative Example compound X2 |
| Example 9 | Example compound 4 | Example compound 3 | Comparative Example compound X2 |
| Comparative Example 1 | Example compound 4 | Comparative Example compound X1 | Comparative Example compound X2 |

(Manufacturing of organic electroluminescence device having plurality of light emitting units) In the organic electroluminescence devices of Example 10, a first electrode EL1 having a thickness of 30 nm was formed using ITO. HAT-CN was deposited to a thickness of 5 nm, and then a hole injection layer (HIL) having a thickness of 10 nm was formed using NPB. A hole transport layer HTL having a thickness of 20 nm was formed using TCTA. In Example Compound 4, a first light emitting layer EML1 doped with 3% of TBP below and having a thickness of 20 nm was formed.

Thereafter, a hole blocking layer HBL having a thickness of 5 nm was formed using Example Compound 1 and an electron transport layer ETL having a thickness of 25 nm was formed by mixing Example compound 1 and LiQ at a ratio of 1:1 to form a first light emitting unit EM1.

Thereafter, BCP was co-deposited with Li at a weight ratio of 97:3 to a thickness of 15 nm as an n-type charge generating layer and HAT-CN was deposited to a thickness of 5 nm as a p-type charge generating layer.

Thereafter, a hole blocking layer HBL having a thickness of 5 nm was formed using Example Compound 1 and an electron transport layer ETL having a thickness of 25 nm was formed by mixing Example compound 1 and LiQ at a ratio of 1:1 to form a second light emitting unit EM2.

Thereafter, BCP was co-deposited with Li at a weight ratio of 97:3 to a thickness of 15 nm as an n-type charge generating layer and HAT-CN was deposited to a thickness of 5 nm as a p-type charge generating layer to form a second charge generating layer CGL2.

Thereafter, a hole injection layer HIL having a thickness of 10 nm was formed of NPB, and a hole transport layer HTL having a thickness of 20 nm was formed using TCTA. In Example Compound 4, a third light emitting layer EML3 doped with 3% of TBP below and having a thickness of 20 nm was formed. Thereafter, a hole blocking layer HBL having a thickness of 5 nm was formed using Example Compound 1, Example Compound 1 was deposited with Liq at a ratio of 1:1 to a thickness of 35 nm, and an electron injection layer EIL having a thickness of 1 nm was formed by using Liq to form a third light emitting unit EM3. Thereafter, a second electrode EL2 having a thickness of 100 nm was formed using Al. Each layer was formed by vacuum deposition.

The organic electroluminescence device of Example 11 was manufactured in the same manner as in Example 10 except that Example Compound 2 instead of Example Compound 1 was used as a material of the hole blocking layer HBL and the electron transport layer HTL.

The organic electroluminescence device of Example 12 was manufactured in the same manner as in Example 10 except that Example Compound 3 instead of Example Compound 1 was used as a material of the hole blocking layer HBL and the electron transport layer HTL.

The organic electroluminescence device of Comparative Example 2 was manufactured in the same manner as in Example 10 except that the hole blocking layer HBL of each of the first to third light emitting units EM1, EM2, and EM3 was formed using Comparative Example X3 instead of Example Compound 1.

(Properties Evaluation of Organic Electroluminescence Device)

1) Evaluation of Lifespan

In order to evaluate the properties of an organic electroluminescence device according to Examples and Comparative Examples, the lifespan of each device was measured.

FIG. 11A shows the degree of luminance reduction over time of the organic electroluminescent device of Examples 1 to 3 and 7 to 9 and Comparative Example 1. FIG. 11B shows the degree of luminance reduction over time of the organic electroluminescent device of Examples 10 to 12 and Comparative Example 2.

Table 3 selectively shows the evaluation values of the organic electroluminescence device of Examples 1 to 3 and 7 to 12 and Comparative Examples 1 and 2. The lifespan of each device is represented by $T_2$, which is the time required for luminance to be reduced from 1000 nit to 2% thereof.

TABLE 3

| Manufacturing example of device | Lifespan ($T_2$, hr) |
| --- | --- |
| Example 1 | 158 |
| Example 2 | 163 |
| Example 3 | 136 |
| Example 4 | 141 |
| Example 5 | 124 |
| Example 6 | 133 |
| Example 7 | 131 |
| Example 8 | 102 |
| Example 9 | 114 |
| Example 10 | 250 |
| Example 11 | 252 |
| Example 12 | 248 |
| Comparative Example 1 | 56 |
| Comparative Example 2 | 200 |

Referring to FIG. 11A, FIG. 11B, and Table 3, it can be confirmed that an organic electroluminescence device according to an embodiment may achieve a long lifespan.

Specifically, Examples 1 to 3 and 7 to 9 exhibit an excellent $T_2$ value of 102 hours to 163 hours. However, Comparative Example 1 exhibits a low $T_2$ value, which is 56 hours. Examples 10 to 12 having the plurality of light emitting units EM1, EM2, and EM3 exhibit an excellent $T_2$ value of 248 hours to 252 hours. However, Comparative Example 2 exhibits a low $T_2$ value, which is 200 hours.

In the case of the organic electroluminescence device of Examples 1 to 3 and 7 to 12, the lifespan of the device is believed to have improved since a polycyclic compound of an embodiment which exhibits excellent durability against holes is used as a material of the hole blocking layer HBL and of at least one of the light emitting layers EML, EML1, EML2, and EML3 and the electron transport layer ETL.

Also, in the case of Examples 1 to 3 and Example 7, the lifespan of the device is believed to have improved since the difference in triplet energy level between a host material of the light emitting layer EML, EML1, EML2, and EML3 and a material of the hole blocking layer material HBL is small, damage to the hole blocking layer HBL by an exciton is mitigated.

Referring to Table 1, in Example 1, the difference in HOMO energy level and the difference in LUMO energy level between Example Compound 4 which is a host material of the light emitting layer EML and Example Compound 1 which is a material of the hole blocking layer HBL are 0.01 eV and 0 eV, respectively, and the difference in $T_1$ energy therebetween is 0.105 eV. In Example 2, the difference in HOMO energy level and the difference in LUMO energy level between Example Compound 4 which is a host material of the light emitting layer EML and Example Compound 2 which is a material of the hole blocking layer HBL are 0.03 eV and 0.02 eV, respectively, and the difference in $T_1$ energy therebetween is 0.1 eV. In Example 3, the difference in HOMO energy level and the difference in LUMO energy level between Example Compound 4 which is a host material of the light emitting layer EML and Example Compound 3 which is a material of the hole blocking layer HBL are 0.02 eV and 0.04 eV, respectively, and the difference in $T_1$ energy therebetween is 0.2 eV.

In Examples 7 to 9, each difference in HOMO energy level, LUMO energy level, and T1 energy level between a host material of the light emitting layer EML and a material of the hole blocking layer HBL is the same as that of Examples 1 to 3.

However, in the case of Comparative Example 1, each energy level difference is greater than that of Examples 1 to 3 and Examples 7 to 9. Specifically, in Comparative Example 1, the difference in HOMO energy level and the difference in LUMO energy level between Example Compound 4 which is a host material of the light emitting layer EML and Comparative Example Compound X1 which is a material of the hole blocking layer HBL are 0.45 eV and 0.09 eV, respectively, and the difference in T1 energy therebetween is 0.93 eV.

In the case of Examples 1 to 3 and Examples 7 to 9, since the difference in triplet energy level between the polycyclic compound included in the hole blocking layer HBL and a host of the light emitting layer EML is small, even though some holes are injected into the hole blocking layer HBL, energy generated by Triplet-Triplet Fusion (TTF) in the hole blocking layer HBL may easily move to the light emitting layer EML, so that triple leakage is believed to have been mitigated to prevent device efficiency from being deteriorated.

3) Evaluation Thin Film Stability

In Example 1 and Comparative Example 3, in order to evaluate the stability of a thin film, each of Example compound 1 and Comparative Example 3 were deposited to 200 Å, and the thin film morphology was observed with an optical microscope. Thin film morphology was compared at an X50 magnification (FIG. 12A 1-1 and 1-2) and an X50 magnification (FIG. 12A 2-1 and 2-2) of the optical microscope.

Referring to FIG. 12A, Image 1-1 and Image 2-1 respectively illustrate the hole blocking layer HBL formed according to Example 1 and Comparative Example 3 enlarged by 50 times, respectively. Image 1-2 and Image 2-2 respectively illustrate Region AA and Region BB enlarged by 50 times, respectively.

Referring to FIG. 12A, when the hole blocking layer HBL was formed using Example Compound 1 substituted with an isopropyl group having a large volume, a uniform thin film was formed, whereas when the hole blocking layer HBL was formed using Comparative Example Compound X3 substituted with a methyl group having a small volume, a non-uniform thin film was formed.

Referring to FIG. 12B, in the case of Example 1, the thin film stability is good, so that a low driving voltage may be achieved. However, in the case of Comparative Example 3, the thin film stability is poor, so that the driving voltage properties are deteriorated.

In the organic electroluminescence device OLED of an embodiment, a polycyclic compound of an embodiment is used to form the hole blocking layer HBL and at least one layer of the light emitting layer EML and the electron transport layer ETL, and thus, a long lifespan of the device may be achieved.

An organic electroluminescence device according to an embodiment of the inventive concept and a display device including the same may achieve a long lifespan.

Although the inventive concept has been described with reference to a preferred embodiment of the inventive concept, it will be understood by those skilled in the art that various changes in form and details may be made therein without departing from the spirit and scope of the inventive concept. Therefore, it is to be understood that the above-described embodiments described above are exemplary and non-limiting in every respect.

What is claimed is:

1. An organic electroluminescence device comprising:
a first electrode;
a second electrode disposed on the first electrode; and
a first light emitting unit disposed between the first electrode and the second electrode, wherein the first light emitting unit includes:
  a first hole transport region disposed on the first electrode;
  a first light emitting layer disposed on the first hole transport region and including a host and a dopant; and
  a first electron transport region disposed on the first light emitting layer and including a hole blocking layer and an electron transport layer disposed on the hole blocking layer, wherein the hole blocking layer, and at least one layer of the first light emitting layer or the electron transport layer include a polycyclic compound represented by Formula 1 below:

[Formula 1]

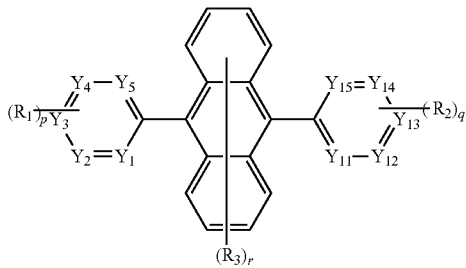

in Formula 1,
each of $Y_1$ to $Y_5$ and $Y_{11}$ to $Y_{15}$ is independently CH or N,
at least four of $Y_1$ to $Y_5$ are CH,
at least four of $Y_{11}$ to $Y_{15}$ are CH, each of $R_1$ $R_2$ and $R_3$ is independently a substituted or unsubstituted alkyl group having 2 to 20 carbon atoms, a substituted silyl group, a substituted boron group, a substituted or unsubstituted aryl group having 6 to 30 ring-forming carbon atoms, or a substituted or unsubstituted heteroaryl group having 3 to 30 ring-forming carbon atoms, or forms a ring by being coupled to an adjacent group, each of p and q is independently an integer of 1 to 5, and
r is an integer of 0 to 8.

2. The organic electroluminescence device of claim 1, wherein the host comprises the polycyclic compound.

3. The organic electroluminescence device of claim 1, wherein the hole blocking layer comprises only the polycyclic compound.

4. The organic electroluminescence device of claim 1, wherein the first light emitting layer, the hole blocking layer, and the electron transport layer comprise the polycyclic compound.

5. The organic electroluminescence device of claim 1, wherein the difference in HOMO energy level and the difference in LUMO energy level between the host and the polycyclic compound is each 0 eV to 0.1 eV.

6. The organic electroluminescence of claim 1, wherein the hole mobility of the polycyclic compound is 0 cm²/Vs to 10¹ cm²/Vs.

7. The organic electroluminescence device of claim 1, wherein the lowest triplet energy level of the polycyclic compound is 1.6 eV to 1.8 eV, and the difference in the lowest triplet energy level between the host and the polycyclic compound is 0 eV to 0.2 eV.

8. The organic electroluminescence device of claim 1, wherein at least one among $R_1$ to $R_3$ is a substituted or unsubstituted pyridine group, a substituted or unsubstituted bipyridine group, a substituted or unsubstituted pyrimidine group, a substituted or unsubstituted triazine group, a substituted or unsubstituted quinoline group, a substituted or unsubstituted quinazoline group, a substituted or unsubstituted quinoxaline group, a substituted or unsubstituted phthalazine group, a substituted or unsubstituted indole group, a substituted or unsubstituted pyrazine group, a substituted or unsubstituted pyridazine group, a substituted or unsubstituted thiophene group, a substituted or unsubstituted oxazole group, a substituted or unsubstituted thiazole group, or a substituted or unsubstituted pyrazole group.

9. The organic electroluminescence device of claim 1, wherein the first light emitting layer emits light having a wavelength region of 440 nm to 490 nm.

10. The organic electroluminescence device of claim 1, further comprising at least one light emitting unit disposed on the first light emitting unit,
wherein the at least one light emitting unit includes:
  a second hole transport region disposed on the first light emitting unit;
  a second light emitting layer disposed on the second hole transport region; and
  a second electron transport region disposed between the second light emitting layer and the second electrode.

11. The organic electroluminescence device of claim 10, wherein the first light emitting unit and the at least one light emitting unit emit blue light.

12. The organic electroluminescence device of claim 1, wherein the polycyclic compound comprises at least one among the compounds represented by Compound group 1 below:

[Compound Group 1]

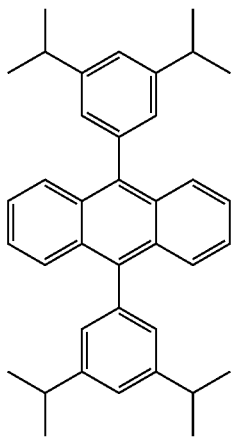
1

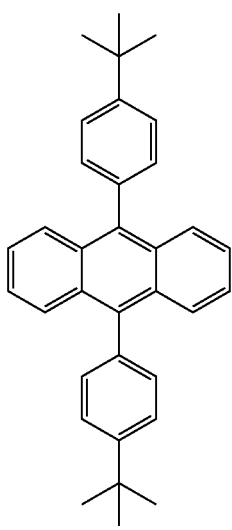
2

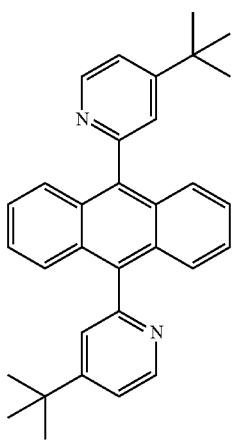
3

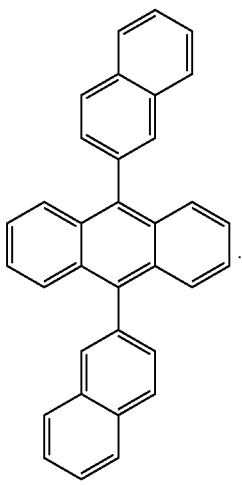
4

13. An organic electroluminescence device comprising:
a first electrode;
a hole transport region disposed on the first electrode;
a light emitting layer disposed on the hole transport region;
an electron transport region disposed on the light emitting layer and including a hole blocking layer and an electron transport layer disposed on the hole blocking layer; and
a second electrode disposed on the electron transport region,
wherein the hole blocking layer and the electron transport layer comprise a polycyclic compound represented by Formula 1 below:

[Formula 1]

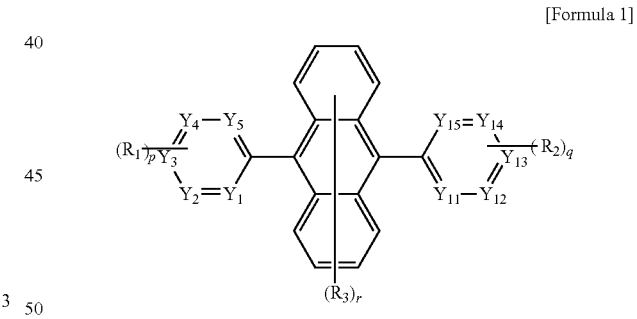

in Formula 1, $Y_1$ to $Y_5$ and $Y_{11}$ to $Y_{15}$ are each independently CH or N,
at least four among $Y_1$ to $Y_5$ are CH,
at least four among $Y_{11}$ to $Y_{15}$ are CH,
each of $R_1$, $R_2$, and $R_3$ is independently a substituted or unsubstituted alkyl group having 2 to 20 carbon atoms, a substituted silyl group, a substituted boron group, a substituted or unsubstituted aryl group having 6 to 30 ring-forming carbon atoms, or a substituted or unsubstituted heteroaryl group having 3 to 30 ring-forming carbon atoms, or forms a ring by being coupled to an adjacent group,
each of p and q is independently an integer of 1 to 5, and
r is an integer of 0 to 8.
14. The organic electroluminescence display device of claim 13, wherein the light emitting layer comprises a host and a dopant, and the difference in HOMO energy level and the difference in LUMO energy level between the host and the polycyclic compound is 0 eV to 0.1 eV.

15. The organic electroluminescence display device of claim 13, wherein the hole blocking layer comprises only the polycyclic compound, and
the electron transport layer further comprises the polycyclic compound and at least one electron transport material.

16. A display device comprising a light emitting element layer including a plurality of organic electroluminescence devices,
wherein each of the organic electroluminescent devices comprises:
a first electrode;
a second electrode disposed on the first electrode;
a plurality of organic layers disposed between the first electrode and the second electrode, wherein the plurality of organic layers comprise:
a hole transport region disposed on the first electrode;
a first light emitting layer disposed on the hole transport region;
an electron transport region disposed on the first light emitting layer and including a hole blocking layer and an electron transport layer disposed on the hole blocking layer, wherein
the hole blocking layer and the electron transport layer comprise a polycyclic compound represented by Formula 1 below:

[Formula 1]

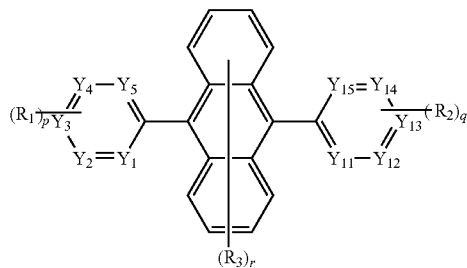

in Formula 1,
$Y_1$ to $Y_5$ and $Y_{11}$ to $Y_{15}$ are each independently CH or N,
at least four among $Y_1$ to $Y_5$ are CH,
at least four among Y11 to Y15 are CH,
each of $R_1$ $R_2$, and $R_3$ is independently a substituted or unsubstituted alkyl group having 2 to 20 carbon atoms, a substituted silyl group, a substituted boron group, a substituted or unsubstituted aryl group having 6 to 30 ring-forming carbon atoms, or a substituted or unsubstituted heteroaryl group having 3 to 30 ring-forming carbon atoms, or forms a ring by being coupled to an adjacent group,
each of p and q is independently an integer of 1 to 5, and
r is an integer of 0 to 8.

17. The display device of claim 16, wherein the organic layers further comprise at least one light emitting layer disposed between the electron transport region and the second electrode.

18. The display device of claim 16, further comprising a light conversion layer disposed on the light emitting element layer,
wherein
the light emitting element layer emits blue light, and
the light conversion layer comprises:
a first light conversion part which absorbs the blue light and emits green light;
a second light conversion part which absorbs the blue light and emits red light; and
a third light conversion part which transmits the blue light.

19. The display device of claim 18, wherein
the first light conversion part comprises a first quantum dot light emitting body which absorbs the blue light and emits red light,
the second light conversion part comprises a second quantum dot light emitting body which absorbs the blue light and emits red light, and
the third light conversion part comprises a base resin and a scattering body dispersed in the base resin.

20. The display device of claim 16, wherein each of the hole transport region, the first light emitting layer, and the electron transport region is included as one layer in the light emitting element layer.

* * * * *